(12) United States Patent
Luo

(10) Patent No.: US 12,399,175 B2
(45) Date of Patent: Aug. 26, 2025

(54) LATERAL FLOW TESTING

(71) Applicant: Zhenguo Luo, Houston, TX (US)

(72) Inventor: Zhenguo Luo, Houston, TX (US)

( * ) Notice: Subject to any disclaimer, the term of this patent is extended or adjusted under 35 U.S.C. 154(b) by 0 days.

(21) Appl. No.: 18/434,947

(22) Filed: Feb. 7, 2024

(65) Prior Publication Data

US 2024/0264157 A1  Aug. 8, 2024

Related U.S. Application Data

(60) Provisional application No. 63/483,783, filed on Feb. 8, 2023.

(51) Int. Cl.
*G01N 33/543* (2006.01)
*G01N 1/02* (2006.01)
*G01N 21/78* (2006.01)
*G01N 33/52* (2006.01)

(52) U.S. Cl.
CPC ......... *G01N 33/54389* (2021.08); *G01N 1/02* (2013.01); *G01N 33/521* (2013.01); *G01N 2001/028* (2013.01); *G01N 21/78* (2013.01)

(58) Field of Classification Search
CPC .... G01N 1/02; G01N 2001/028; G01N 21/78; G01N 33/521; G01N 33/54389
See application file for complete search history.

(56) References Cited

U.S. PATENT DOCUMENTS

| | | | |
|---|---|---|---|
| 4,833,088 A | 5/1989 | Desimone et al. | |
| 2002/0001539 A1* | 1/2002 | DiCesare | B01L 3/5029 422/174 |
| 2004/0184954 A1 | 9/2004 | Guo | |
| 2004/0237674 A1 | 12/2004 | Wu | |
| 2006/0024843 A1 | 2/2006 | Lee et al. | |
| 2016/0025752 A1 | 1/2016 | Santiago et al. | |
| 2021/0291165 A1 | 9/2021 | Rothberg et al. | |
| 2021/0291177 A1 | 9/2021 | Rothberg et al. | |
| 2021/0292825 A1 | 9/2021 | Rothberg et al. | |
| 2021/0292855 A1 | 9/2021 | Rothberg et al. | |
| 2022/0249073 A1* | 8/2022 | Charlton | G01N 1/02 |

FOREIGN PATENT DOCUMENTS

| | | | |
|---|---|---|---|
| AU | 2021200665 | 3/2021 | |
| CN | 105973883 B | * 11/2018 | ............... G01N 1/10 |
| WO | 94/04916 | 3/1994 | |
| WO | WO 2024167988 A1 | * 8/2024 | |

OTHER PUBLICATIONS

Machine translation of CN 105973883 B, published Nov. 20, 2018.*
International Search Report and Written Opinion for PCT/US24/14713, dated Jun. 24, 2024.

* cited by examiner

*Primary Examiner* — Galina M. Yakovleva
(74) *Attorney, Agent, or Firm* — Sheehan Phinney Bass & Green PA

(57) ABSTRACT

A test device includes a base holding at least one test strip in a plane. A buffer storage container is adjacent a first end of the test strip. A top of the buffer storage container is higher than the plane of the base. A frangible seal extends across the top of the buffer storage container. A transfer passage between the top of the buffer storage container and the first end of the test strip.

18 Claims, 24 Drawing Sheets

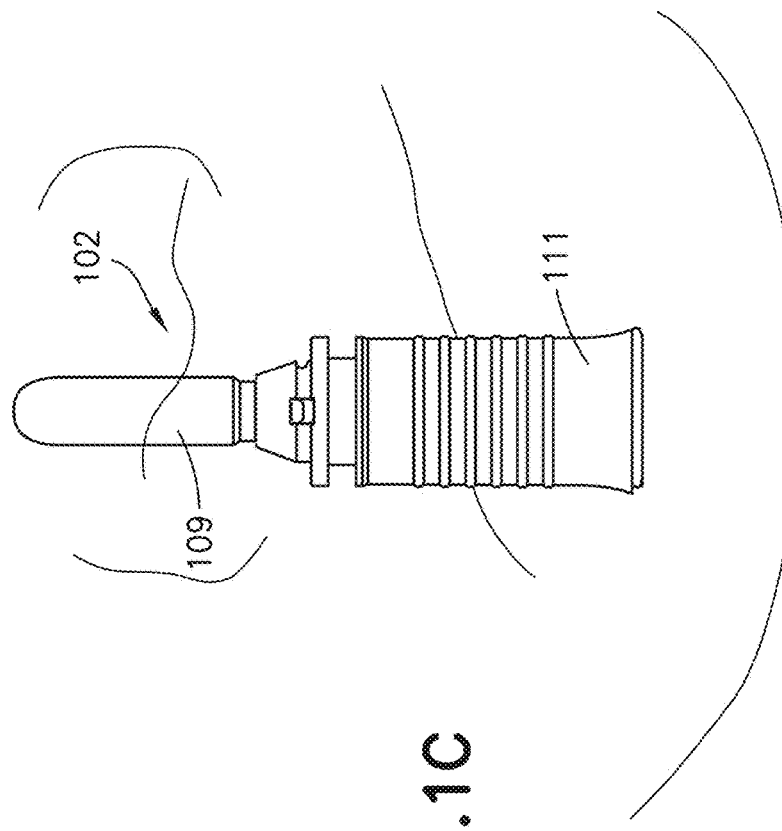
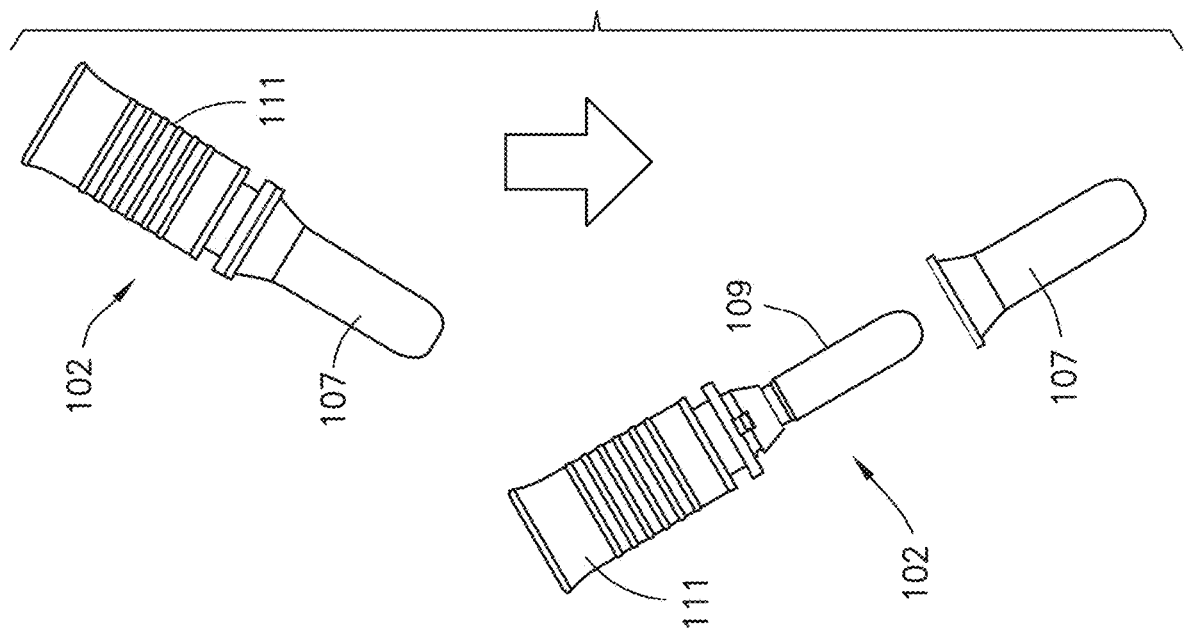

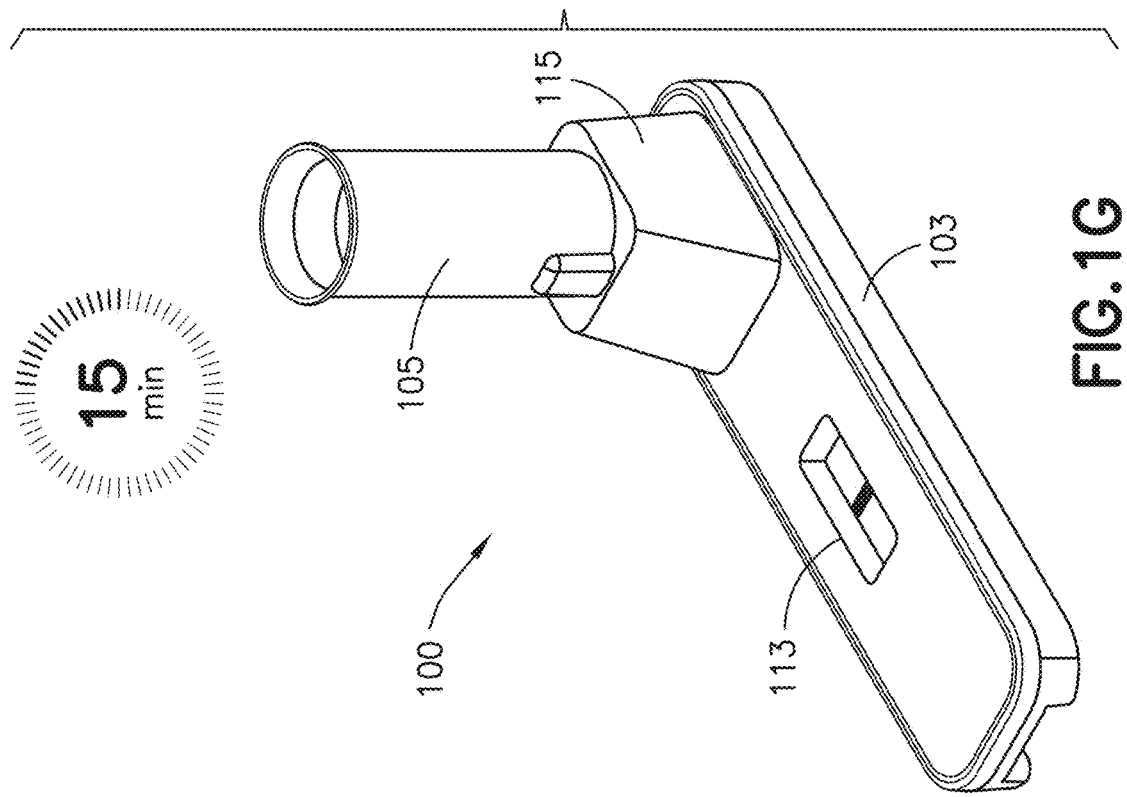
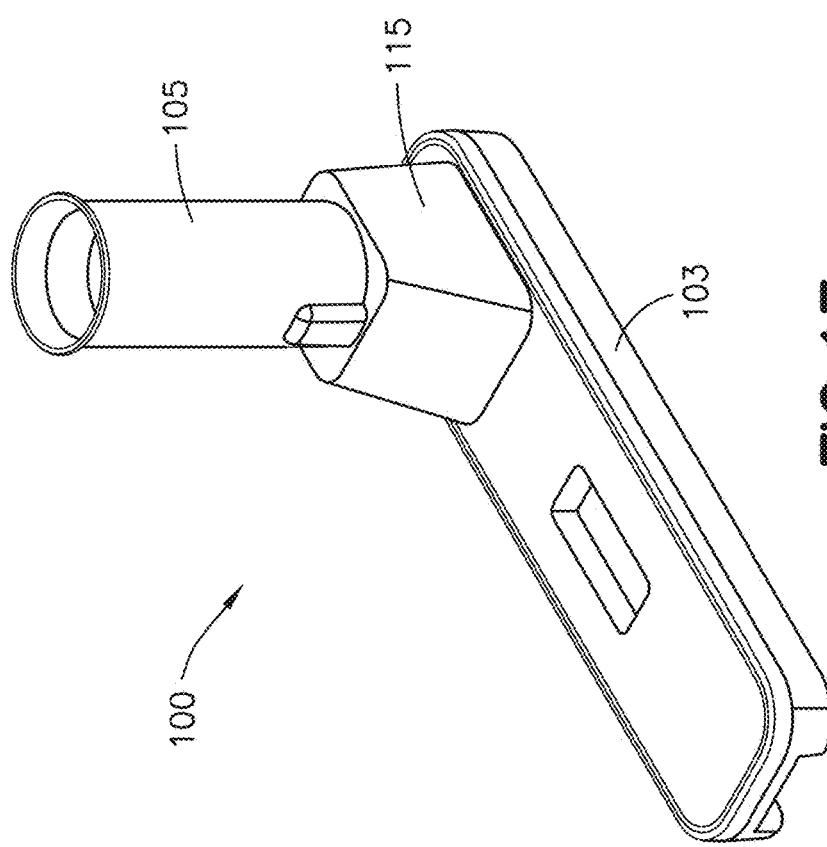
FIG. 1F
FIG. 1G

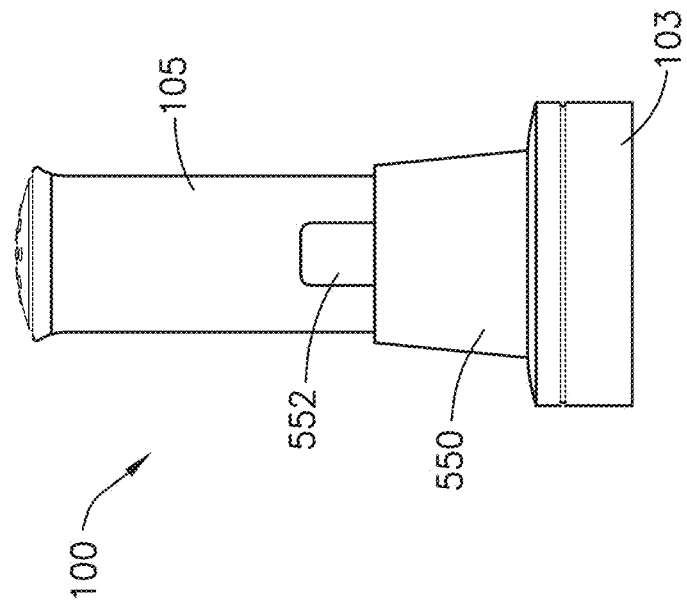
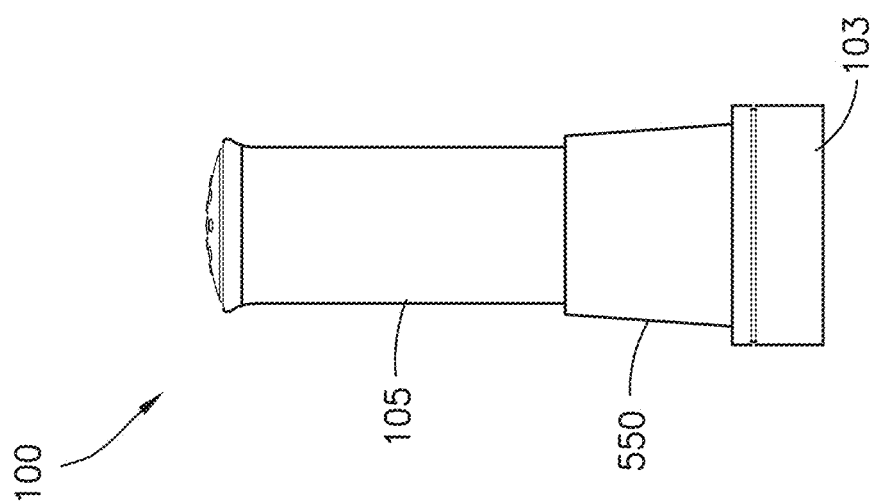

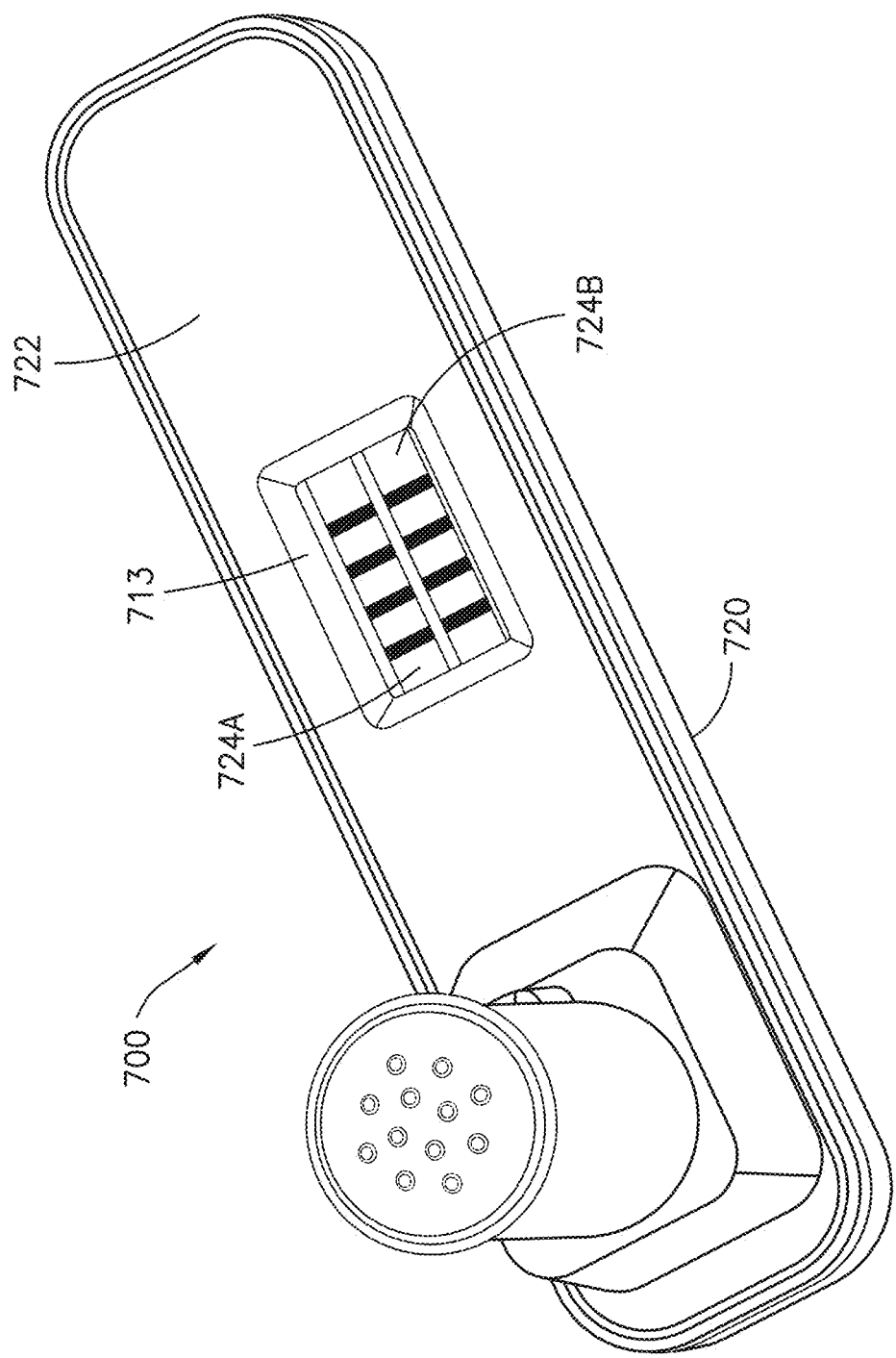

STEP 02

OPEN & POWER ANALYZER

STEP 05

COLLECT THE SAMPLE

STEP 04

UNCAP THE SWAB

LATERAL FLOW TESTING

CROSS-REFERENCE TO RELATED APPLICATION(S)

This application claims the benefit of U.S. Provisional Patent Application Ser. No. 63/483,783, filed Feb. 8, 2023, and entitled Lateral Flow Testing. The disclosure of the prior application is incorporated by reference herein in its entirety.

FIELD OF THE INVENTION

This application relates to lateral flow testing and, more particularly, relates to a testing device for conducting lateral flow testing and associated processes.

BACKGROUND

Lateral flow tests are easy-to-use diagnostic devices that can confirm the presence or absence of various conditions (e.g., in a human body), based on sample (e.g., saliva, mucus, etc.) taken, for example, from the human body. Common types of lateral flow tests includes pregnancy tests and Covid Antigen tests. Lateral flow tests typically have one or more test result lines and one or more control lines that, if rendered visible (or otherwise observable), indicate that the test has worked properly. Lateral flow tests are widely used across many industries for point of care, as well as at-home testing. They can be performed by professionals, trained lay users, or patients. Some tests have visible (to human eye) lines, while others have invisible lines (e.g., fluorescence lines) that only are observable, detectable, or recognizable by a paired reader/analyzer. The latter tends to be more sensitive.

In addition to testing for conditions in human bodies, lateral flow tests it can be used in veterinary diagnostic testing. Outside of diagnostic testing, lateral flow rapid tests can also be used for water quality testing, powder testing (for example, dissolve cocaine powder into buffer, test with a strip to see if there's Fentanyl in it), wipe/surface testing (for example, airport security checks for cocaine residues in a carry-on bag).

Improvements in lateral flow testing, and associated devices, are desired.

SUMMARY OF THE INVENTION

In one aspect, a test device includes a base holding at least one test strip in a plane. A buffer storage container is adjacent a first end of the test strip. A top of the buffer storage container is higher than the plane of the base. A frangible seal extends across the top of the buffer storage container. A transfer passage between the top of the buffer storage container and the first end of the test strip.

In another aspect, a testing system includes a test device with a sample collector. As above, the test device includes a base holding at least one test strip in a plane. A buffer storage container is adjacent a first end of the test strip. A top of the buffer storage container is higher than the plane of the base. A frangible seal extends across the top of the buffer storage container. A transfer passage between the top of the buffer storage container and the first end of the test strip.

In yet another aspect, a method of testing includes providing a test device, providing a sample collector, collecting the sample to be tested on a swab portion of the sample collector; and urging the swab portion of the sample collector through the frangible seal and into the buffer container. As above, the test device includes a base holding at least one test strip in a plane. A buffer storage container is adjacent a first end of the test strip. A top of the buffer storage container is higher than the plane of the base. A frangible seal extends across the top of the buffer storage container. A transfer passage between the top of the buffer storage container and the first end of the test strip. Moreover, the sample collector includes a handle portion and the aforementioned swab portion, which is connected to the handle portion.

In some implementations, one or more of the following advantages are present.

For example, as a form of lateral flow testing, the systems and techniques disclosed herein are easy to use and provide rapid results (in 5-20 min typically). A major benefit of lateral flow tests is fast and cheap, as a screening device.

For example, testing devices and processes disclosed herein provide quick reliable testing, often in a comfortable, at-home environment. The testing typically involves lateral flow technologies with configurations that simplify testing protocols involving such technologies considerably. Testing may be easier, more user-friendly, and less prone to human error than existing comparable testing devices and processes. Fewer steps may be required of the user while testing and, therefore, unnecessary complications may be avoided.

Moreover, testing may involve less direct handling of fluids and other testing components. The transfer of buffer liquid (and its mixing with the test sample), for example, from an initial buffer storage container to a lateral flow test strip may happen quickly, easily, conveniently, and automatically. Thorough mixing of a collected sample with the buffer liquid can happen quickly, easily, conveniently, and automatically as well. The risk of spilling the buffer liquid and specimen sample mixture, for example, may be reduced considerably. Moreover, with the risk of spilling reduced, the risk of contamination may be reduced as well, particularly in HIV testing of whole blood, for example.

Testing may occur, in a typical implementation, with a lateral flow test strip lying horizontally, which results in fast, accurate results. Moreover, multiple different types of tests may be performed using a single testing device and test process. The multiple different tests may be performed using multiple different test strips in a single testing device. Those different test strips may be arranged side-by-side and may produce results that are able to be viewed (or detected by a companion reader/analyzer) side-by-side simultaneously. This may make it easier and quicker for a person to see and understand the results of the testing. In various implementations, it may be possible to integrate two, three, four, or more test strips (e.g., of different types) on the same one cassette (i.e., in the same single test device). This enables running multiple different tests simultaneously. In some such implementations, all strips can run from one sample well from the same pool of sample specimen. This helps ensure that the different strips receive relatively consistent and homogenous specimen samples. In these implementations, all the strips are drawing from the same pool of liquid mix (sample/buffer). Moreover, test strips typically are laid flat when a test is conducted. Lateral flow action works better this way compared to configurations where there is a vertical flow direction. This also makes the test device easier to integrate with certain reader/analyzer.

A reader may be used to capture an image of the test and/or control line(s) on one or more test strips in a single test device and process the image to determine an outcome (positive or negative) for the test, based on the image. In those instances, if there is more than one test, then the one or more test strip outputs can be captured in an image (e.g., by a camera built into the reader) and processed to determine the outcome for all tests simultaneously. Incorporating a reader in a test can provide clear benefits including, for example, elimination of human interpretation error by ways of using machine/AI's result interpretation; and the ease of (sometimes mandatory) result reporting to health authorities such as the CDC and the HHS.

The systems and techniques disclosed herein may facilitate capturing a high quality, clear image for the reader to process. This is because the viewing opening, through which a test results image can be captured, is uncovered, therefore, eliminating the possibility of some unwanted glare or other visual obstruction happening by virtue of a reflective covering (e.g., glass or plastic). In the case of visible lines, for example, a flash may cause glare or other visual obstructions; in the case of non-visible lines such as fluorescence, it is a UV lamp/LED that generally flashes on the line(s) and gets captured by the camera, then the image(s) get processed and analyzed for result interpretation. Having the opening uncovered eliminates any image quality problems that may be caused by a reflective covering for example.

In a typical implementation, the test device has a built-in buffer, so it eliminates the need to handle/transport small liquid when trying to conduct a test.

Compared to certain pen-type test devices (that have built-in swabs), the swab is a separate module, not integrated with the test device (or the test strips in the test device). This makes it easier to perform the necessary sterilization process on the swab during production. Additionally, as compared to some pen-type devices, implementations of the present devices and systems eliminate glare problems that may be present when a test device is paired with a reader/analyzer that uses a flash (visible light or UV, etc.). Additionally, as compared to some pen-type test devices, implementations of the test device disclosed herein are designed to operate with the strips in a horizontal (rather than vertical) direction, which avoids the needs for lateral flow to have to fight against gravity. Moreover, there tends to be more space available for multiple, side-by-side strips to be arranged in implementations of the test device disclosed herein than in a pen-type tester, which has more limited strip space (e.g., typically only allowing for up to 3 strip slots). The top piece and bottom piece of the test device creates a tight reservoir to hold any solution (e.g., buffer and specimen sample mixture), if the cassette is sideways for a short period of time during test, it will not affect the result. The buffer liquid is in a sealed reservoir/container initially. As and after the swab containing specimen punctures through the seal, the specimen gets mixed with the buffer to create a solution which will then flow onto the strip(s). Moreover, as the swab collector punctures through the frangible seal (e.g., aluminum foil), a seal ring ensures that the solution (i.e., a mixture of the buffer liquid and the sample specimen) can only flow down through the narrow transfer channel (see, e.g., arrows in FIG. 4B) into a reservoir which then flow onto the strip(s). In a typical implementation, the seal ring is very important. It prevent the mixture solution (buffer liquid and specimen sample) from flowing upwards through the "chimney" (of the hollow tubular portion) and leaking outside. This is important for a variety of reasons including sanitary/contamination reasons but also to ensure the solution can only go through the channel onto the well that connects the receiving end of the strip(s). Because of the O-ring on the handle, the mixture solution has nowhere to go but through the transfer passage (to the test strip(s)). Also, referring, for example, to FIGS. 3A and 3B (discussed herein in detail), a cavity formed by mating 222 and 220, specifically around frames 334, 336, and 340, typically holds a temporary "pool" of mixture solution, because the absorb pad of the strips cannot absorb the solution fast enough. In the event that the test device is knocked over during testing, for example, the cavity together with the O-ring makes sure the solution is (and stays) in there (e.g., inside the test device), and the knocking over does not affect the performance of test (e.g., if the test device is sideways or upside down for a short period of time).

Buffer liquid typically does not have any target test substance. In a typical implementation, its purpose is to dissolve a target substance and sometimes prepare the target substance (such as breaking the cell wall) to be ready to react with reagents such as antibodies/antigens on the test strip(s).

The buffer container typically has a very similar inner diameter as the outer diameter of the swab tip, and the inner wall of the buffer container typically has bumps or other protrusions. This ensures the swab tip is tightly squeezed as it is being pushed into the buffer container, to make sure the sample collected on the swab tip is adequately washed by the buffer. And the solution can only go up through the swab tip again to flow through the channel into reservoir connecting the strips, again washing any residue samples collected by the swab.

Other features and advantages will be apparent from the description and drawings, and from the claims.

BRIEF DESCRIPTION OF THE DRAWINGS

FIGS. 1A-1G are perspective views showing an exemplary sequence of steps for conducting a test using a test kit that includes an implementation of a test device for conducting lateral flow testing.

FIGS. 5A-5G are different views showing an implementation of a test device.

FIG. 7A is a perspective view showing an alternative implementation of a test device.

Like reference characters refer to like elements.

DETAILED DESCRIPTION

This application relates to test devices and methods used in connection with testing for the presence or concentration of certain molecules (e.g., proteins, antigens, etc.) in a fluid sample (e.g., from a person's body or elsewhere). Some examples of the fluid samples include mucus from the person's nose or throat, a sample of saliva, urine, stool samples in the case of FOB (fecal occult blood) testing (which should be considered a fluid sample in this context, particularly since it will be a fluid after mixing with buffer), vaginal secretion, lesions (for monkey pox rapid tests for example), and a wide variety of other fluid samples.

In one specific implementation, the test device is intended for Covid antigen or Flu AB testing, either used as a standalone test device (with results being visually interpreted by naked eye), or together with a reader that interprets the result (e.g., by machine/artificial intelligence). However, the test device can be expanded into and/or used for testing for other infectious diseases, drugs of abuse, pregnancy, and with all kinds of bodily fluid such as saliva, urine, nasal mucus, throat mucus, feces, sweat, etc. The test device can also be used for surface testing, wastewater testing, and environmental testing. In some implementations, surface testing is like a "wipe test", where one runs a collection swab across a surface like a tabletop or steering wheel or luggage surface and runs the test strip to see if there are target drug substances for example, on those surfaces.

FIGS. 1A-1G show a sequence of steps for conducting a Covid-19 Antigen test using a test kit that includes an implementation of the test device 100. In a typical implementation, the test kit will be provided inside a sealed package 101 and optionally within an outer box that surrounds the package.

Figure 1A:
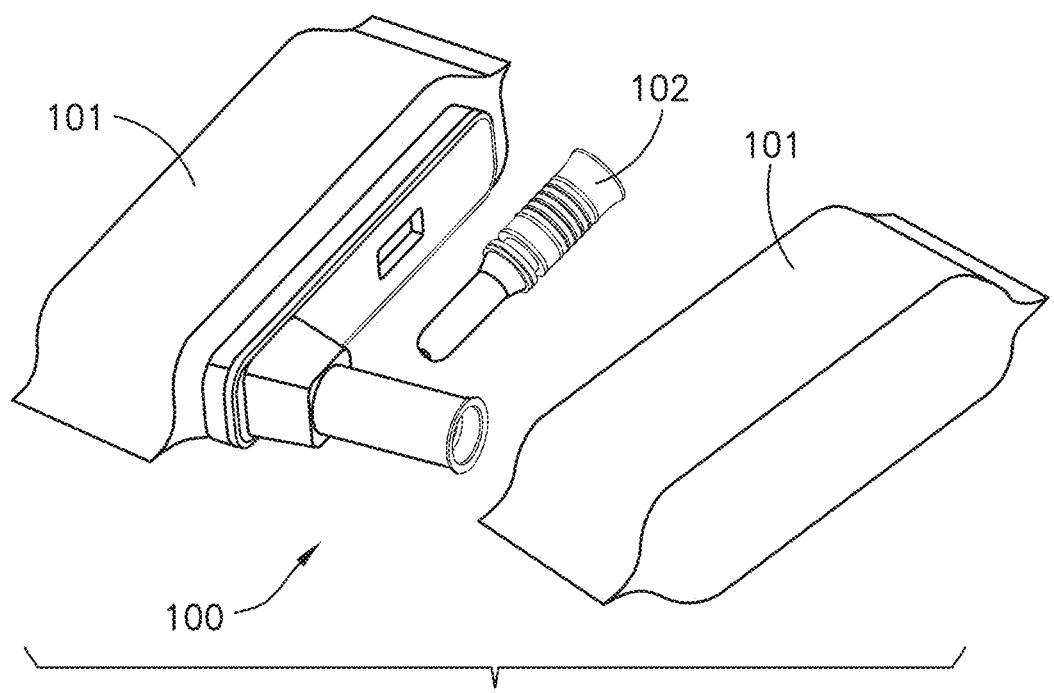

FIG. 1A represents the first step in the illustrated process, in which a user would unseal the package 101 and remove its components, which include the test device 100 and a sample collector 102. In some implementations, such as the one represented in the illustrated figure, these are the only items provided in the package, and the only items required to perform the Covid-19 Antigen test. Notably, there is no separate container to store a buffer, or any other test fluids, for the Covid-19 Antigen test. The buffer, in a typical implementation, is completely contained within a sealed buffer container that is adhered to, formed integrally to, or otherwise connected to or part of the test device 100 itself. Moreover, there is no separate component for holding test strip(s). Any test strips are contained within the test device 100 itself as well. Nor are there any other components. The test kit is relatively straightforward and easy-to-use in this regard.

Figure 1B:
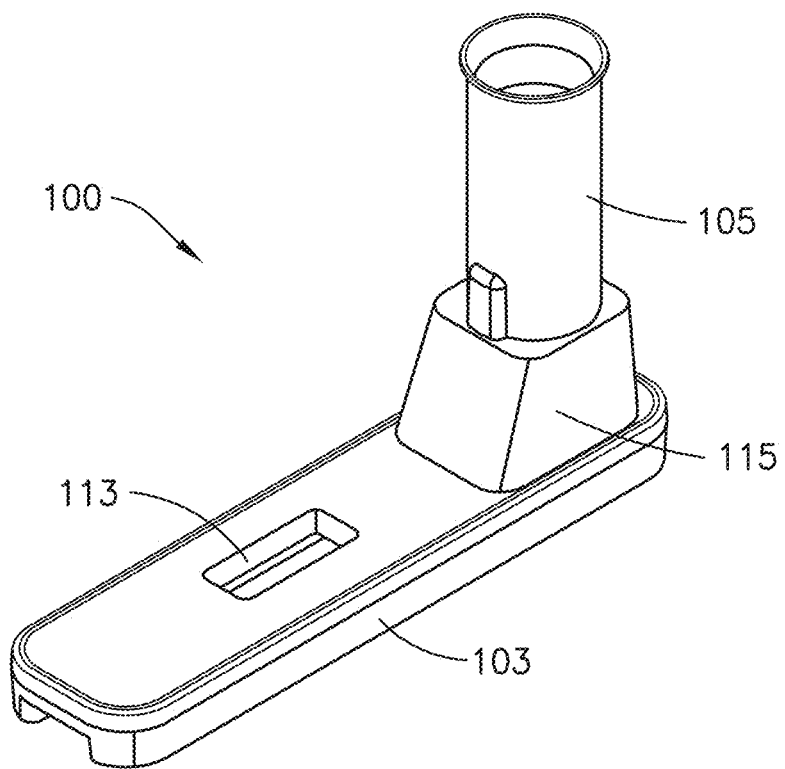

FIG. 1B shows the next step in the illustrated process, in which the user places the test device 100 on a flat surface, such as a tabletop, a countertop, or the like. The test device 100 is configured to sit on the flat surface as shown with its base 103 resting on and in direct physical contact with the flat surface and a hollow tubular portion 105 of the test device 100 extending vertically upward near one end of the base 103. The hollow tubular portion 105 of the test device 100 has an axis about which the hollow tubular portion 105 is symmetrical. That hollow tubular portion axis is perpendicular to the plane in which the test strip (224, see FIG. 2) is supported by base 103. A buffer storage and transfer section 115 connects the base 103 to the hollow tubular portion 105. The buffer storage and transfer section 115, in an exemplary implementation, accommodates a buffer container that stores buffer liquid, at least prior to testing and transfers the buffer liquid (while mixing in a specimen sample) onto one or more test strips inside the test device automatically as a user conducts the test. A test result viewing opening 113 is provided in an upper surface of the base 103 that enables viewing (or otherwise detecting) test results that appear (e.g., as one or more lines) at the conclusion of a test on one or more test strips that are inside the base 103 of the test device 100 but visible through the opening 113.

FIG. 1C shows the next step in the illustrated process, in which the user removes a protective cap 107 from the sample collector 102. The sample collector 102 has a handle 111 and a swab 109 connected to the handle 111. Removing the cap 107 reveals the swab 109 at the distal end of the sample collector 102. The swab includes a wad of cotton, or the like, wrapped around a short rod made of plastic or other rigid material.

Figure 2:
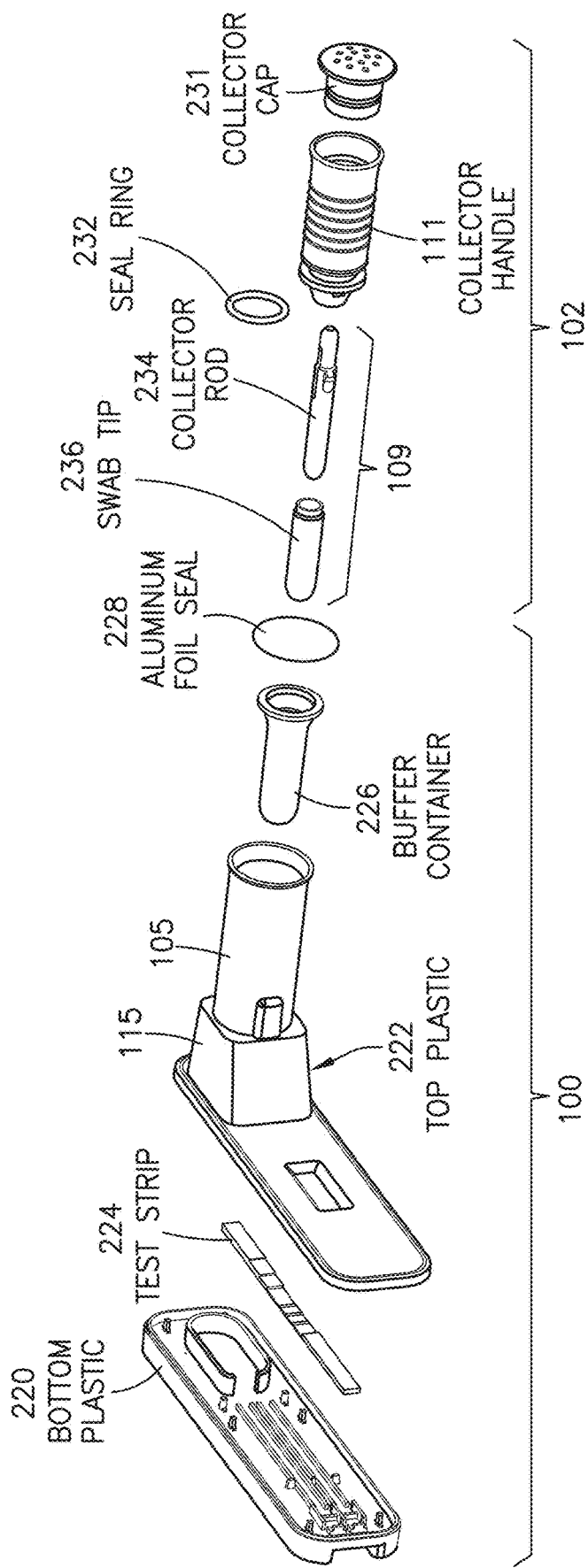
FIG. 2 is an exploded view of an exemplary implementation of a test device and a sample collector.

FIG. 2 is an exploded view of an exemplary implementation of a test device 100 and a sample collector 102.

According to the illustrated implementation, the test device 100 includes a housing that includes a bottom piece 220 and a top piece 222, which are both made of plastic in the illustrated implementation, as well as a buffer container 226, and a frangible seal 228 for the buffer container, which is aluminum foil in the illustrated implementation.

In a typical implementation, the bottom piece 220 and the top piece 222 mate together (e.g., with a friction or snap fit) to form the base 103 of the test device 100 and the upward extension from the base 103 (which includes the hollow tubular portion 105 and the buffer storage and transfer station 115). A test strip 224 is provided and contained between the bottom piece 220 and the top piece 222 of the test device 100. More specifically, the test strip sits atop the bottom piece 220 of the housing and beneath the top piece 222 of the housing.

Figure 3A:
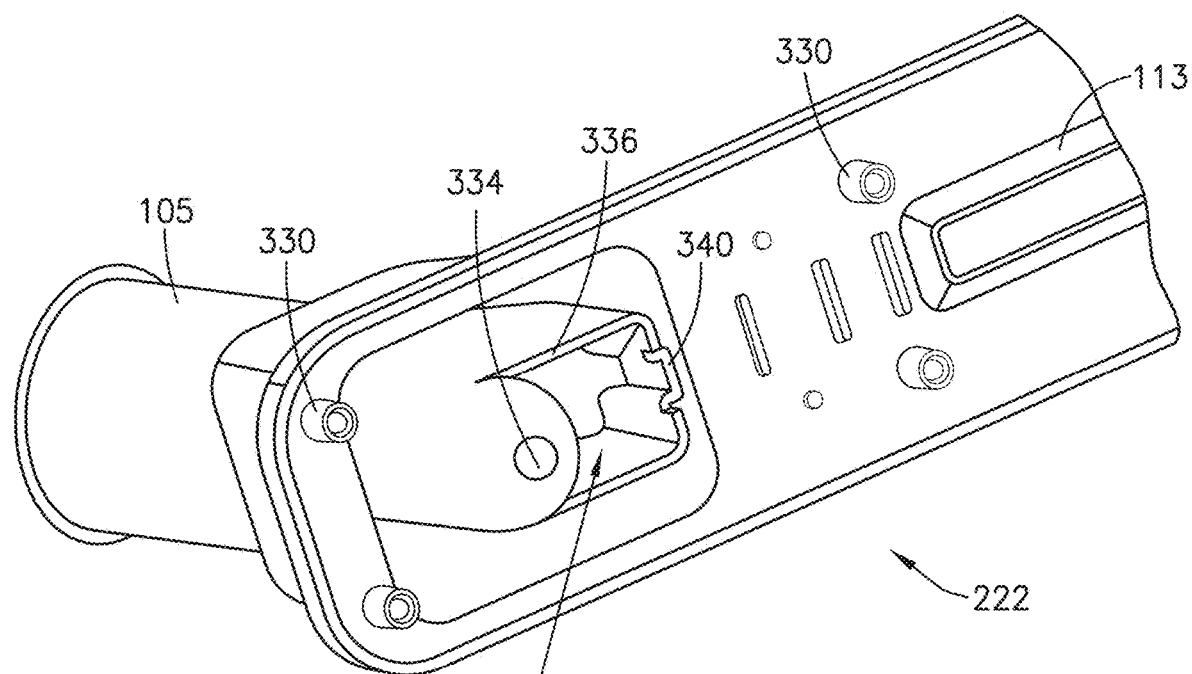
FIG. 3A is a partial detailed perspective view showing lower surfaces of a top piece of a housing of the exemplary implementation of the test device.
Figure 3B:
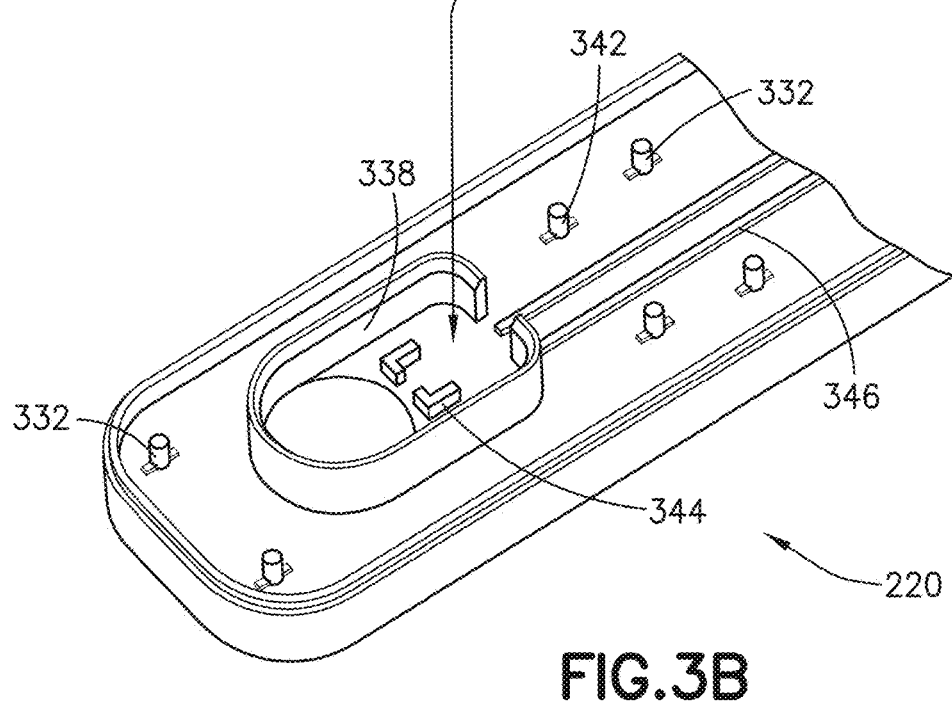
FIG. 3B is a partial detailed perspective view showing upper surfaces of the bottom piece of the housing of the exemplary test device.

FIG. 3A is a partial detailed perspective view showing lower surfaces of the top piece 222 of the housing and FIG. 3B is a partial detailed perspective view showing upper surfaces of the bottom piece 220 of the housing. These FIGS. 3A and 3B), together, indicate how some of the geometries on these surfaces are shaped and able to fit together in assembly. In this regard, according to the illustrated implementation, the lower surfaces of the top piece 222 of the housing define multiple small, hollow, open-ended, cylindrical tubes 330 that extend in a downward direction (i.e., toward the bottom piece 220 of the housing). Moreover, the upper surfaces of the bottom piece 220 of the housing define multiple small cylindrical projections 332 that extend in an upward direction (i.e., toward the top piece 222 of the housing). In a typical implementation, at least some of the projections 332 extend into, and frictionally engage, corresponding tubes 330 to join, and hold, the top piece 222 and bottom piece 220 together (with a test strip 224 therebetween).

The lower surfaces of the top piece 222 of the housing also define an outer surface of a housing 334 that contains the buffer container 226, and a frame 336 that extends from the outer surface of the buffer container housing 334. The frame 336, together with a portion of the outer surface of the buffer container housing 334, defines a transfer passage, through which the liquid analyte passes after exiting the buffer container 226 to reach the test strip 224. When the top piece 222 and the bottom piece 220 are mated to one another, the rounded outer surface of the housing 334 for the buffer container sits inside a corresponding concave, bowl-shaped surface on the bottom piece 220 of the housing.

Moreover, when the top piece 222 and the bottom piece 220 are mated to one another, the frame 336 on the top piece 222 sits within, and frictionally mates with, a corresponding frame 338 on the bottom piece 220 of the housing. When so mated, most of the lower surface of the frame 336 comes into direct physical contact with an upper surface of the bottom piece 220 within the frame 338. However, the frame 336 has one raised part 340 that has a bottom surface that is raised relative to the rest of the frame 336. The bottom surface of this raised part 340 does not physically contact the upper surface of the bottom piece 220 when the top piece 222 and bottom piece 220 are mated. Instead, the raised part 340 leaves a space (through which the test strip can pass) between the upper surface of the bottom piece 220 and the lower surface of the raised part 340. The raised part 340 of the frame 336 aligns with an opening 342 in the frame 338 when mated together. The test strip passes through this opening 342 as well. In a typical implementation, the passage for the test strip (formed by the raised part 340 of frame 336 and the opening 342 in frame 338) is small. Often, this passage is just large enough to snugly accommodate the passage of the test strip 224. In some implementations, the smallness of this passage helps control (or slow) the flow of liquid analyte away from the very beginning of the test strip 224.

The upper surface of the bottom piece 220 also has a set of frame elements 344 for receiving and helping to ensure proper positioning and alignment of one end of the test strip 224 within the test device 100. More specifically, the frame elements 344 are configured and positioned to receive the first end of the test strip (e.g., the end that has or is near the sample pad). These frame elements 344 are mirror-image L-shaped frame elements in the illustrated implementation. In a typical implementation, the upper surface of the bottom piece 220 also has a corresponding set of frame elements (that may form a mirror image of frame elements 344) near a distal end of the base of the test device. The corresponding set of frame elements would be configured and positioned to receive the second end of the test strip (opposite the first end). The upper surface of the bottom piece 220 also has pair of spaced-apart, parallel guide ribs 346 that extend, longitudinally, down the base 103 to receive, therebetween, and hold, in proper place, the test strip 224.

Referring again to FIG. 2, the buffer container 226 in the illustrated implementation is a tubular container with a rounded bottom and a top that flares radially outward. The buffer container 226 is sized to fit inside the tubular portion 105 and the buffer storage and transfer section 115 of the test device 100. In a typical implementation, the rounded bottom fits snugly within a corresponding rounded surface at the bottom of the and the buffer storage and transfer section 115 of the test device 100. Moreover, the outwardly-flared top of the buffer container 226 sits atop a corresponding annular lip inside the tubular portion 105 of the test device 100. The buffer container 226 may be held in place at the bottom of the tubular portion 105 of the test device 100 by friction fit and/or with an adhesive or by any other means.

When assembled, the buffer container 226 contains the liquid buffer. The top of the buffer container 226 gets covered and sealed by the aluminum (frangible) seal 228, which may be adhered to the upper, flat surface of the outwardly-flared top of the buffer container 226. In a typical implementation, the aluminum seal 228 is sturdy enough to maintain a seal on the buffer container 226 during normal handling during storage and transport. Nevertheless, the aluminum seal 228 is fragile enough that a user is able to compromise the seal by pushing the collector 102 down on the aluminum seal 228 until the seal breaks, pulls off of the buffer container 226, or otherwise clears a path for motion and/or fluid flow into/out of the buffer container 226.

Still referring to FIG. 2, the sample collector 102 includes a collector handle 111 with a collector cap 231, a seal ring 232 that fits around the collector handle 111, a collector rod 234 that attaches to the collector handle 111, and a swab tip that fits over a distal end of the collector rod 234. The collector handle 111, in the illustrated implementation, is a hollow tubular structure, with gripping ridges on an outer surface thereof. The collector cap 231 is a plug that fits into the opening at the larger diameter end of the collector handle 111. The seal ring 232 is an O-ring that is configured to sit within an annular ring in an outer cylindrical surface of the collector handle 111, near the collector rod 234 and swab tip 236. The collector rod 234 is a rigid rod (or elongate, shaped element) that fits into and engages (either frictionally, with a snap fit, or using an adhesive, etc.) with an opening at an end of the collector handle 111 opposite the collector cap 231. The swab tip 236 fits over and substantially (e.g., more than 90%) or entirely covers the portion of the collector rod 234 that extends out from the collector handle 111. The swab tip 236 is preferably soft and may be made of cotton or other soft, similar material. In some implementations, the swab tip 236 is held in place over the collector rod 234 by a friction fit and/or with an adhesive material.

FIG. 1D shows the next step in the illustrated process (after the FIG. 1C step), in which the user collects a sample of mucus for testing. In the illustrated implementation, the user does this by inserting the distal tip 109 of the sample collector 102 inside his or her nostril and rubbing the inner surfaces of the user's nasal passageways. In some implementations, the user may collect from only one nostril. In some implementations, the user may collect from both nostrils. The user typically grips the handle 111 while performing these actions.

Figure 1E:
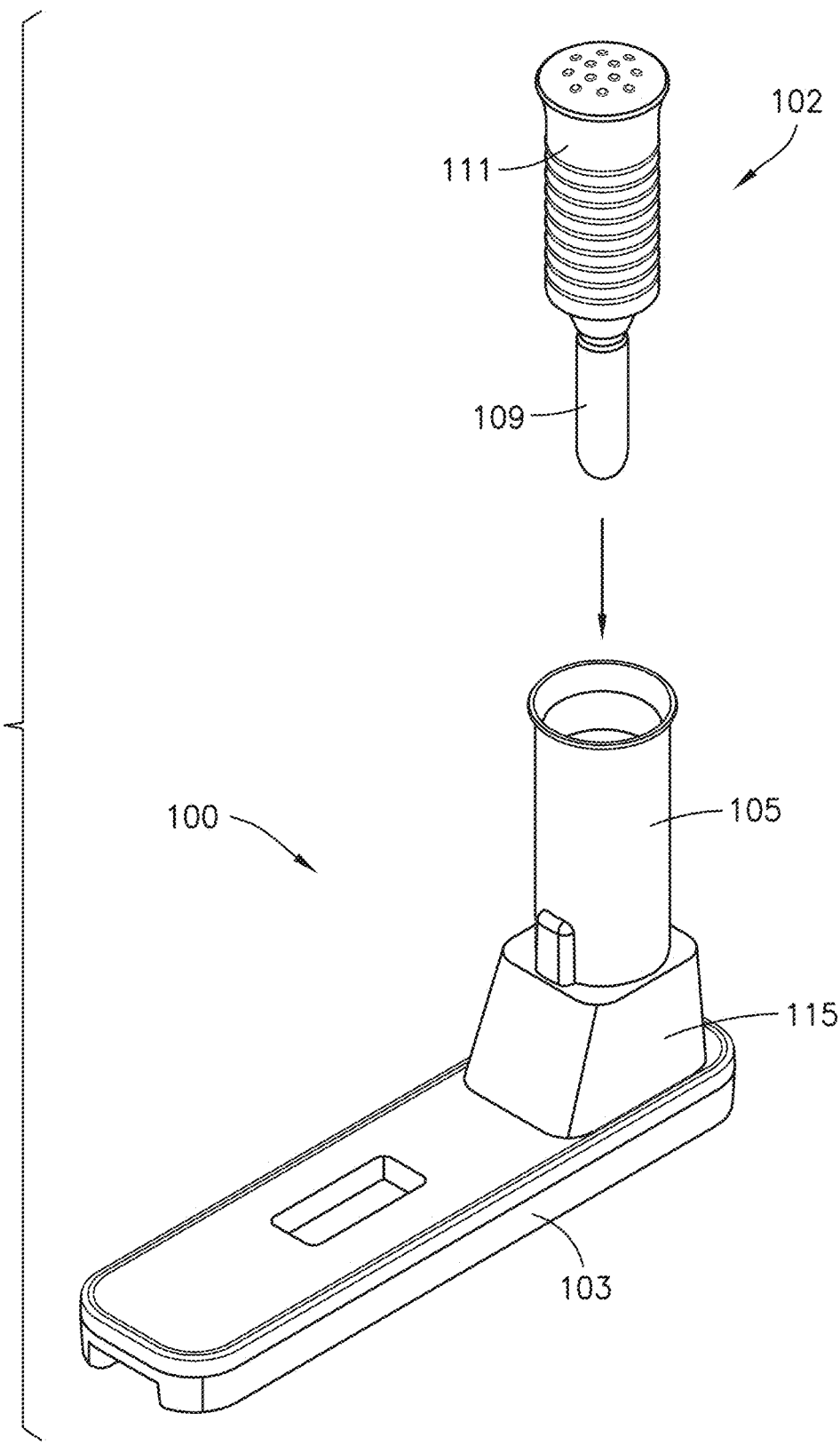

FIG. 1E shows the next step in the illustrated process, in which the user inserts the sample collector 102, with the collected mucus (sample) on its swab 109, into the test device 100. More specifically, in the illustrated implementation, the sample collector 102 is inserted, swab-side-down, into the hollow tubular portion 105 of the test device 100. This may be done while the test device 100 remains in place on the flat surface beneath it. Eventually, the distal tip of the sample collector 102 reaches the frangible seal 228 covering the buffer container 226 inside the test device 100. The buffer container 226 contains a liquid buffer for the Covid-19 Antigen test. Once the distal tip of the sample collector 102 reaches the frangible seal 228, continued downward movement of the sample collector 102 relative to the test device 100 applies pressure to and eventually ruptures the frangible seal 228. Once the frangible seal 228 has been ruptured, continued downward movement of the sample collector 102 relative to the test device moves the swab 109 into the buffer container 226 and eventually to the very bottom of the buffer container 226, displacing the buffer fluid as it continues moving downward.

Figure 4A:
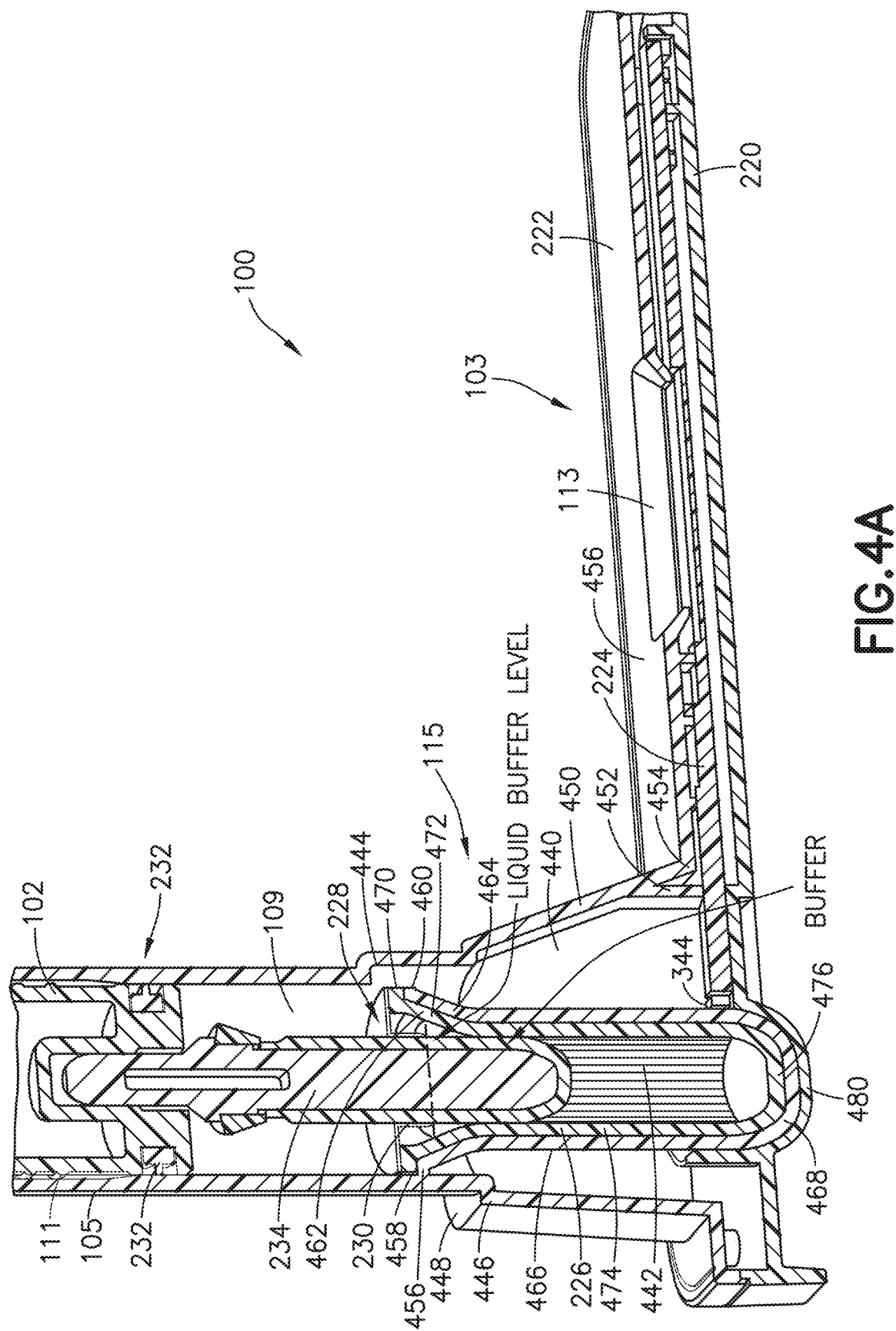
FIGS. 4A and 4B are cross-sectional views showing an example of a sample collector moving downward inside the tubular portion of the test device.
Figure 4B:
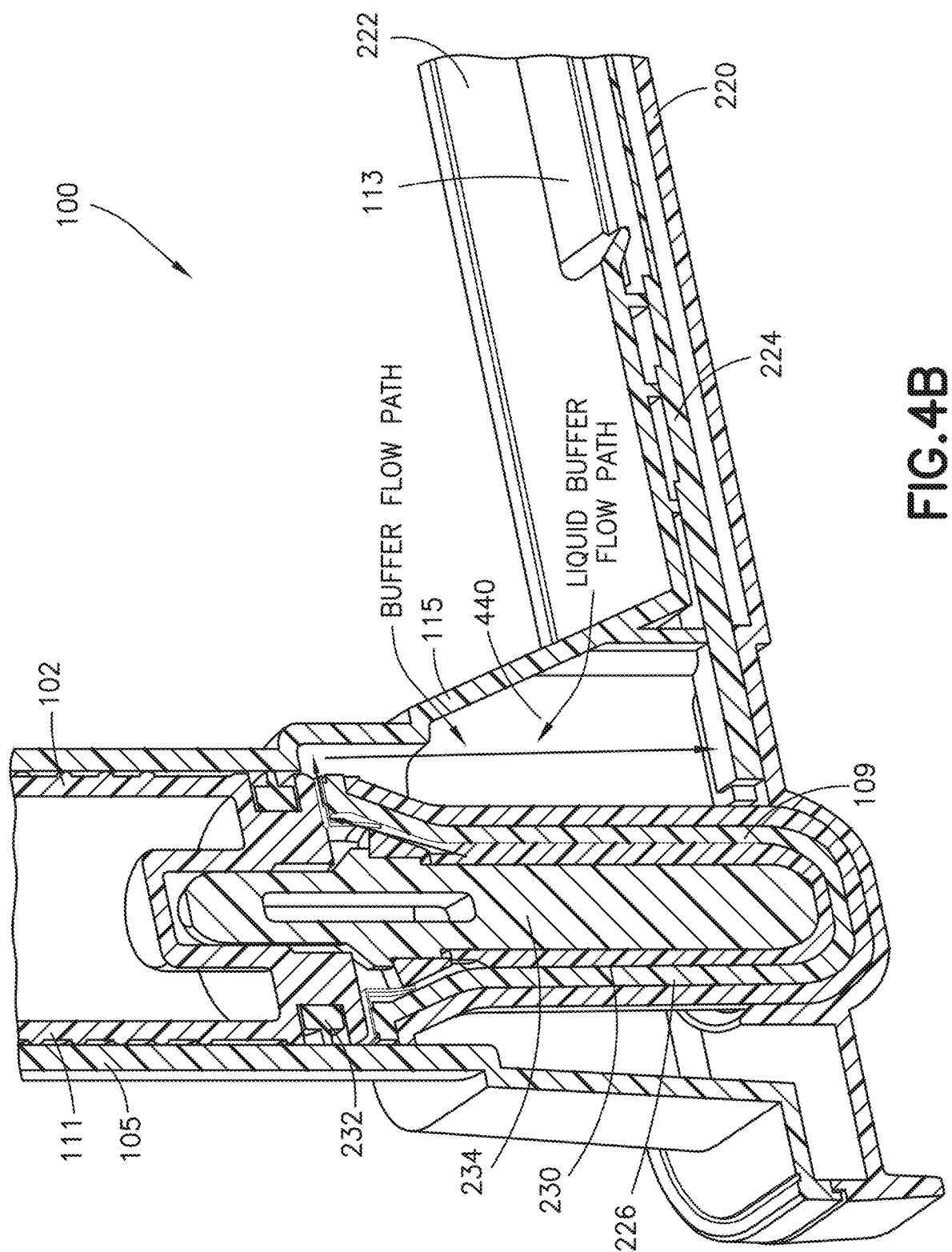

FIGS. 4A and 4B are cross-sectional views showing an example of a collector 102 moving in a downward direction inside the tubular portion 105 of the test device 100. More specifically, the distal tip of the collector 102 in both figures already has pushed through and broken or otherwise compromised the frangible seal 228 on the buffer container 226. Moreover, the distal tip of the collector 102, namely, a portion of the collector rod 234 and the swab tip 230 covering the collector rod 234 have passed beyond the compromised frangible seal 228 and into the buffer container 226.

In a typical implementation, including the one represented in the FIGS. 4A and 4B, the swab 109 at the distal end of the sample collector 102 has a diameter that makes it a tight fit when the swab 109 (i.e., the collector rod 234 and swab tip 230) is pressed down into the buffer container. In some implementations, in fact, the collector rod 234 and swab tip 230 are sized so that, once inserted into the lower narrower portion of the buffer container 226, the entire outer circumferential perimeter of the swab tip 230 contacts, and remains in contact with, the inner surface of the buffer container 226. This, typically, causes the swab tip 230 to be squeezed and compressed a bit as it is pushed down into the narrower, bottom portion of the buffer container (as shown in FIG. 4A, for example).

As the sample collector 102 continues moving down into the buffer container, the swab 109 comes into contact with, and begins to displace, the buffer liquid inside the buffer container 226. The displaced buffer liquid, mixed with the specimen sample, has nowhere else to go except up and around the sides of the sample collector 102 (and swab 109) as the swab 109 pushes deeper into the buffer container. Since there is a tight fit between the swab 109 and the buffer container 226, at least a portion of the displaced buffer liquid mixes with the specimen sample as it flows up and around the sample collector 102 squeezes past and/or through the swab 109. This facilitates the transfer of the specimen sample from the swab 109 to the liquid buffer. Additionally, in some implementations, the inner surface of buffer container 226 has ribs or grooves 442 that the swab 109 rubs against as the swab 109 moves through the buffer container 226. This rubbing action further facilitates the transfer of the sample from the swab 109 into the liquid buffer.

As the swab 109 moves further down into the buffer container 226, displacing the liquid buffer, the level of liquid buffer in the buffer container 226 continues to rise. Eventually, as the swab 109 continues moving down into the buffer container, the level of liquid buffer in the buffer container 226 gets so high that some of the liquid buffer, with a portion of the sample, begins to spill over the upper edge of the buffer container. (See, e.g., the Liquid Buffer Flow Path labeled in FIG. 4B). The liquid buffer mixture that spills over the upper edge of the buffer container 226 falls through a transfer passage 440 in the test device 100 and onto the first end of the test strip 224 (e.g., where the sample pad may be located). As the swab 109 continues moving down into buffer container 226, more and more of the liquid buffer mixture spills out of the top of the buffer container 226, through the transfer passage 440 and onto the test strip 224. The path of liquid buffer past the swab tip 230, out of the buffer container 226, through the transfer passage 440, and onto the test strip 224 is represented by a series of arrows (labeled Liquid Buffer Flow Path) in FIG. 4B. Eventually, by the time the swab 109 has been fully inserted into the buffer container 226 (again shown in FIG. 4B), most (or at least a substantial portion) of the liquid buffer will have been pushed out of the buffer container and down onto the test strip.

Meanwhile, as the collector 102 (with its swab 109) moves downward inside the tubular portion 105 of the test device 100, the annular seal ring 232 (sitting in an annular groove in the outer surface of the collector handle 111) maintains a seal against the inner surface of the tubular portion 105 of the test device. This seal (between the annular seal ring and the inner surface of the tubular portion 105) prevents the liquid buffer from flowing past it.

The base 103 of the illustrated test device 100 supports the test strip 224 in a horizontal plane and the receiver compartment supports the buffer container 226 in an upright manner with its frangible seal at the top of the buffer container 226. The collector 102, in the illustrated implementation, moves down into and through the buffer container 226 in a downward direction that is perpendicular to horizontal plane of the test strip 224. The collector 102 is guided by (and seals against, with O-ring 232) the cylindrical inner surface of the hollow tubular portion 105 of the test device 100. In a typical implementation, the buffer container 226 is symmetrical about a vertical axis that extends through the middle of the buffer container 226 and perpendicular to the horizontal plane of the test strip 224.

FIG. 1F shows the sample collector 102 fully inserted into the test device 100. With the sample collector 102 so positioned, only the very top of the handle portion of the sample collector 102 is visible at the very top of the opening in the hollow tubular portion 105 of the test device 100. At this point in the process, all of the analyte sample that is to be delivered onto the test strip will have been delivered onto the test strip and that portion of analyte sample will be working its way through the test strip 224 to the portion of the test strip under the window 113 that will reveal test results.

The test strip 224 is flat and is supported by and within the base 103 of the test device 100. Preferably, the test device 100 is resting on a horizontal support surface while the test is being performed. In that case, the test strip, too, would be lying in a horizontal plane substantially parallel to the horizontal support surface. The first end of the test strip 224, where the liquid buffer/sample mixture ("analyte") first contacts the test strip is near the buffer container 226 and the test strip 224 extends in a linear fashion radially outward and away from the buffer container 226. The second end of the test strip 224 (opposite the first end of the test strip) sits at a distal end of the base 103 of the test device.

The test strip itself can have any one of a variety of different configurations. In one example, the test strip has, in this order, a sample pad, a conjugate pad, a nitrocellulose membrane, a test line, a control line, and final absorbent pad or wick. In such implementations, the analyte sample first contacts the test strip at the sample pad travels along the test strip (e.g., via capillary action) across all of the other test strip segments until reaching the final absorbent pad or wick.

In general, the sample pad acts as a sponge. It receives the analyte sample that spills out of the buffer container and is able to hold some amount of the analyte sample. As the sample pad becomes saturated, the analyte sample begins to flow from the sample pad and onto the conjugate pad. The conjugate pad stores conjugated labels and antibodies configured such that, if the target is present in the analyte sample, the conjugated antibodies and labels bind to the target and continue to migrate along the test strip. As the analyte sample moves along the strip, binding reagents on the nitrocellulose membrane bind to the target at the test line causing a colored line (or some other visual or otherwise detectable indicator) to appear on the test strip. The control line becomes visible (or otherwise detectable) to show that the analyte sample has flowed across the test strip and that the bio-molecules in the conjugate pad are active. After passing these reaction zones, the analyte sample enters the final absorbent pad or wick and is simply absorbed there.

The portion of the test strip that has the test line and the control line sits below and is exposed for viewing through a test results viewing opening in the base 103 of the test device 100. In a typical implementation, the test results viewing opening is simply an opening in an upper surface of the base 103 that allows a user to see both the test line and the control line, if one or both end up becoming visible (or otherwise detectable) during the course of a test, or not. Moreover, in a typical implementation, the test results viewing opening is simply an opening in the upper surface of the base 103 (i.e., it has no physical covering or protective film to protect or in any way cover, obstruct, or interfere with viewing the test line and control line portions of the test strip inside the base 103). This open uncovered opening facilitates clear, unobstructed viewing or detecting of the test and/or control lines, which can be particularly important in instances where a reading machine that operates by capturing an image of the test line and control line portion of the test strip and processing that image (with one or more computer processors) to identify the presence (or absence) of a visible (or otherwise detectable) test and/or control line, is involved. Since such reading machines capture an image of the test line and control line portion of the test strip, any covering over the test line and control line portion of the test strip (even a transparent covering) may compromise the resulting image quality and, therefore, the accuracy of the reader's processing conclusions. Having no window or other covering over the test line and control line portion of the test strip (e.g., between the test strip and the input lens of any image capture component in the aforementioned reading machine) avoids these potential technical problems.

FIG. 1G indicates that after some period of time (15 minutes in the illustrated implementation), the test will be considered completed and one or more lines should have appeared on the test strip (if the test was successful) and be visible through the test results opening in the base 103 of the test device 100. In a typical implementation, if the test line and the control line both appear, then the test result should be considered positive; if only the control line appears (but not the test line), then the test result should be considered negative; if the control line does not appear (whether the test line appears or not), the test should be considered invalid. In the illustrated implementation, only the control line is visible, indicating a negative test result.

FIGS. 4A and 4B reveal additional details about both the top piece 222 and bottom piece 220 of the test device 100.

For example, the wall of the hollow tubular portion 105 forms a straight tube that extends down to a first jut out 444 that forms a small internal pocket to form part of the internal transfer passage 444 to accommodate the flow of buffer liquid and specimen sample mixture that spills over the upper edge of the buffer container 226. This first jut out 444 extends towards and faces the same direction that the base 103 extends away from the buffer storage and transfer section 115 of the test device 100. Aside from the first jut out 444, the rest of the tubular portion 105 extends to the bottom of the first jut out 444 following the same tubular downward path that it followed above the first jut out 444. The side wall of the first jut out 444 extends in a downward direction, parallel to the aforementioned tubular path that is followed by the wall of the hollow tubular portion 105.

At the bottom of the first jut out 444 there is a second jut out 446. The second jut out extends in a radially outward direction to form an external platform 448 that is horizontally disposed and that extends around an entirety of that portion of the test device 100. The platform 448 is substantially rectangular (e.g., rectangular but with rounded edges) and lies in a plane that is horizontal and parallel to the upper surface of the base 103. (See also FIG. 2).

Returning to FIGS. 4A and 4B, at the outer edge of the second jut out 446, the wall turns downward. Three of the four walls that extend downward from the outer edges of the substantially rectangular platform 448 are substantially perpendicular to the horizontal platform 448 (or angled outward no more than a few degrees, e.g., typically, less than 5 degrees). The front wall 450 that extends downward from the front edge of the substantially rectangular platform 448 has a more significant outward angle. This provides room within the test device 100 to accommodate the buffer liquid transfer passage 440. The angle of the front wall 450, relative to vertical, can range between 10 and 30 degrees. In some implementations, the angle is about 20 degrees.

An extension 452 extends off of an inner surface of the angled front wall 450 close to the bottom of the angled front wall 450, in a vertical downward direction. This extension 452 is configured so that its distal bottom tip ends up close to bottom piece 220 when the top piece 222 and bottom piece 220 are coupled together. In a typical implementation (e.g., like the one shown), the amount of space between the distal bottom tip of the extension 452 and the closest part of the bottom piece 220 is large enough to allow for the test strip 224 to extend through the space. However, in a typical implementation, the space is not any larger than that. The extension essentially forms at least part of the front end of the transfer passage 450.

The four walls that extends down from the platform 448 end in a bend 454 to form a section 456 of the test device 100 that is disposed in a substantially horizontal orientation and that forms part of the base 103 of the test device 100. The test results viewing opening 113 is formed in this section 456 of the test device 100 and extends through this section 456 of the test device 100 from its outer surface to its inner surface, with angled walls as represented in FIG. 4A, for example.

The top piece 222 in the illustrated implementation also has a section that forms a receiver compartment for receiving and holding the buffer container 226. In this regard, an extension 456 extends off an internal surface of the test device 100 just below the first jut out 444 near the bottom of the hollow tubular portion 105. This extension 456 extends in a radially internal direction and is disposed in a horizontal plane to form a flat, horizontal, annular, upward-facing surface 458 to support the outwardly-flared upper lip of the buffer container 226.

A space 460 is provided between an outer edge of the extension 456 that forms the annular surface 458 and an internal surface of the first jut out 444. This space 460 forms part of the transfer passage 440 for the buffer liquid and specimen sample mixture that spills out of the top of the buffer container 226. Aside from the space 460 provided between the outer edge of the extension 456 and the internal surface of the first jut out 444, the rest of the outer periphery of the extension 456 extends out from and is in direct physical contact with the inner surface of the test device 100.

An inner edge of the horizontally-disposed extension 456 forms a circle. There is a downward bend 462 at this circular inner edge that leads into a flared segment 464 that extends in a downward, inward direction at an angle. The angle, in a typical implementation, is less than 25 degrees from vertical and in some implementations may be between 10 degrees and 20 degrees.

At the bottom of the flared segment 464 is another bend that leads into a cylindrical segment 466 that extends in a vertically downward direction. The bottom 468 of the receiver compartment, in the illustrated implementation, is curved and closed off.

Thus, the receiver compartment in the illustrated implementation is near the bottom of the hollow cylindrical portion 105 of the test device 100. It is also immediately adjacent to the transfer passage 440. It is contoured to receive and hold the buffer container 226. More specifically, as shown in FIGS. 4A and 4B, when assembled, the outwardly-flared upper lip 470 of the buffer container 226 is in direct physical contact with the annular surface 458 of extension 456. An angled portion 472 of the buffer container 226 is in direct physical contact with the flared segment 464 of the receiver compartment. A cylindrical portion 474 of the buffer container 226 is in direct physical contact with the cylindrical segment 466 of the receiver compartment. A rounded bottom 476 of the buffer container 226 is in direct physical contact with the bottom 468 of the receiver compartment.

In a typical implementation, the buffer container 226 is held in place within the receiver compartment with an adhesive that may be provided between any one or more of the available physical contact surfaces. In some implementations, the buffer container 226 may be held in place via a press fit (e.g., with friction). Prior to use, when the buffer container 226 is in place in the receiver compartment, the buffer container 226 is completely sealed—e.g., with the frangible seal 228 that extends across the open top of the buffer container 226. The frangible seal, in a typical implementation, is held in place on the buffer container 226 with an adhesive (e.g., between the frangible seal and the annular upper surface of the buffer container 226). Other methods of adhering are possible as well.

The bottom piece 220 of the test device 100 includes a bowl-shaped segment 480 configured to surround and be in direct physical contact with the curved bottom 468 of the receiver compartment. As previously mentioned, the bottom piece 220 also has frame elements 344 on its upper surface that hold (and help ensure proper positioning of) the test strip 224. One of the frame elements 344 is shown in FIG. 4A adjacent to the receiver compartment. As can be seen, one end of the test strip 224 contacts that frame element 344. Since the frame element 344 is adjacent to the receiver compartment and the frame element 344 essentially marks the position of one end of the test strip 224, that end of the test strip 244 also is essentially adjacent to the receiver compartment. Moreover, as can be seen in the illustrated implementation, that end of the test strip 224 is at the bottom of the transfer passage and a portion of that end of the test strip 224 is directly beneath the outer edge of the outwardly-flared upper lip 470 of the buffer container 226. Moreover, a portion of that end of the test strip 224 is directly beneath the first jut out 444 of the test device 100. The lower piece 220 also has a support extension that extends in a downward direction around a periphery of the base 103.

Figure 5C:
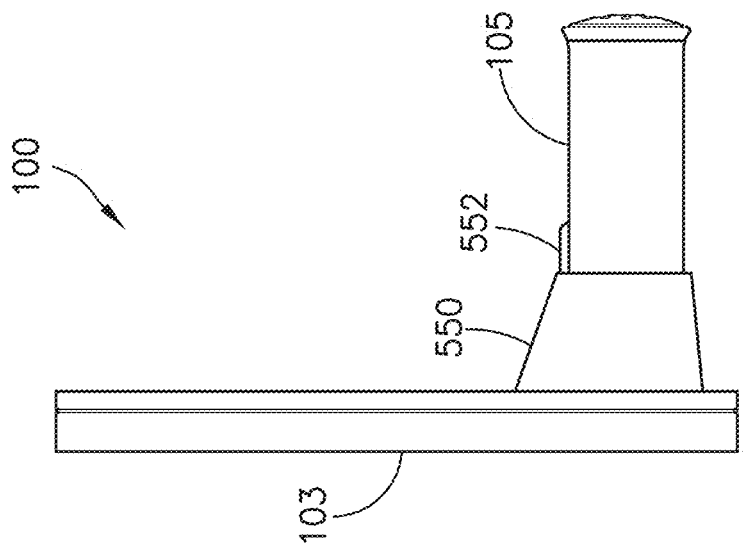
Figure 5B:
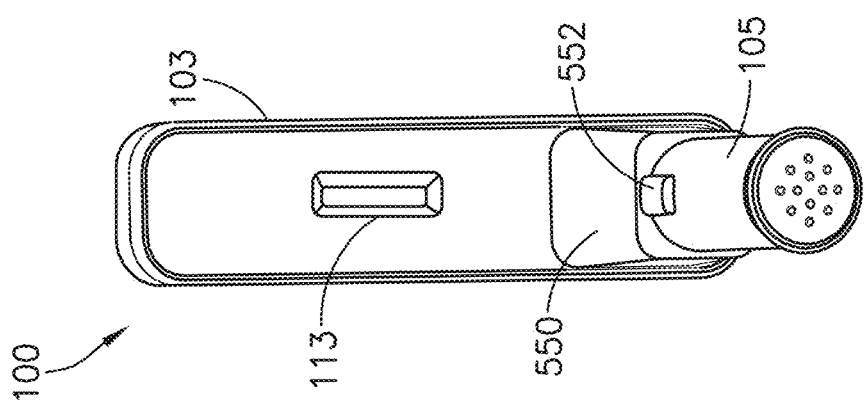
Figure 5A:
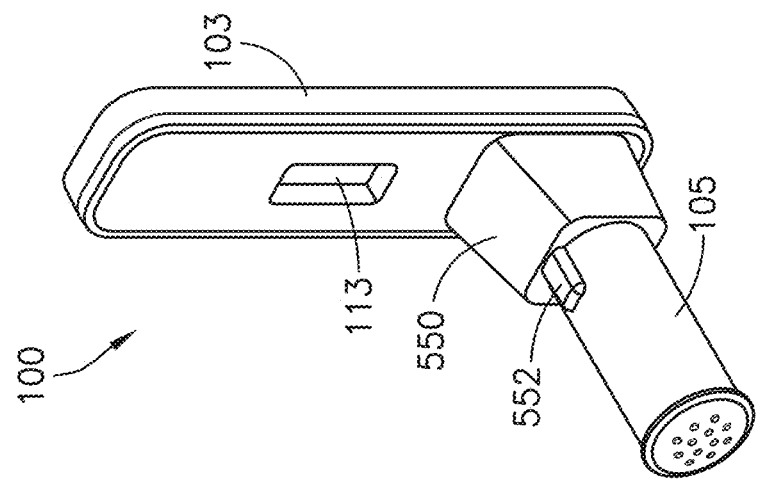
Figure 5E:
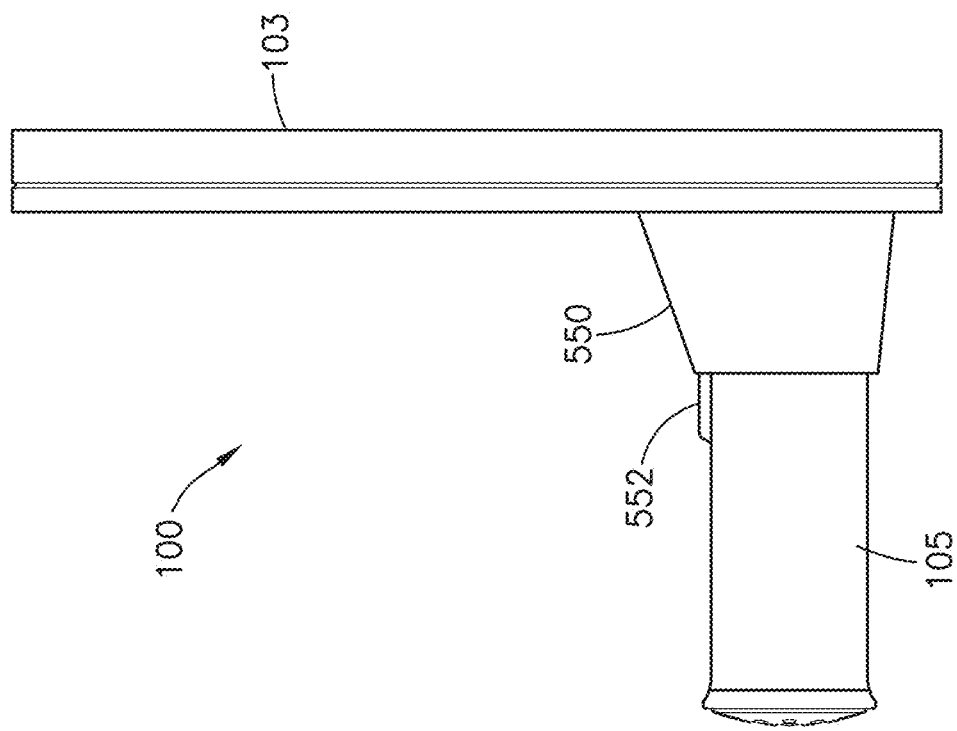
Figure 5D:
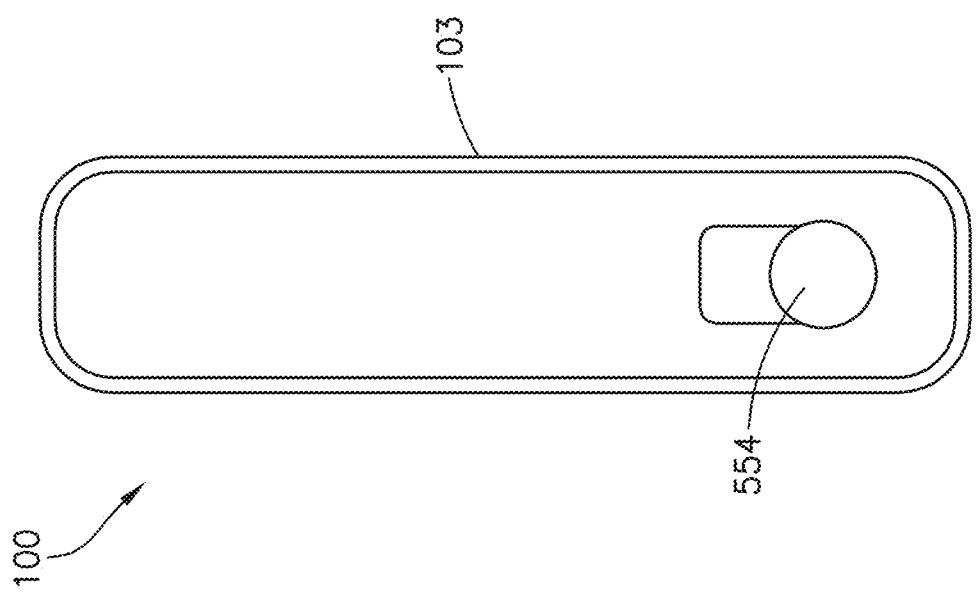

FIGS. 5A-5G show multiple views, from different viewing perspectives, of an implementation of test device 100. More specifically, FIG. 5A shows a perspective view of the test device 100, FIG. 5B shows a top view of the test device 100, FIG. 5C shows a left side view of the test device 100, FIG. 5D shows a bottom view of the test device, FIG. 5E shows a right side view of the test device 100, FIG. 5F shows a rear view of the test device 100, and FIG. 5G shows a front view of the test device 100.

In each figure, various parts of the test device 100, visible in the figure, are labeled. These include, for example, the base 103, the hollow tubular portion 105, and the test result viewing opening 113. Also labeled is a base structure 550 (at the bottom of the hollow tubular portion 105) and a small outward projection 552 in the hollow tubular portion 105 just above the base structure 550. The base structure 550 has a perimeter that is dimensionally larger than the circumference of the hollow tubular portion 105. The base structure 550 also has a forward surface that slopes down from the top of the base structure 550 to the base 103 of the test device 100 and in the direction in which the base 103 extends away from the hollow tubular portion 105. The small outward projection 552 is positioned on the outer surface of the hollow tubular portion 105 at a side of the hollow tubular portion 105 that faces the direction in which the base 103 extends away from the hollow tubular portion 105. Thus, the small outward projection 552 is on the same side of the hollow tubular portion 105 as the sloped surface of the base structure 550.

Cross-referencing FIGS. 4A and 4B with FIGS. 5A-5G, it can be seen that these structures (i.e., the small outward projection 552 and the base structure 550, particularly the sloped surface of the base structure 550) accommodate and form the internal transfer passage 440, through which the buffer liquid and specimen sample mixture travels between the upper edge of the buffer container 226 and the test strip 224.

Cross-referencing FIGS. 4A and 4B with FIG. 5D (the bottom view of the test device 100), it can be seen that a rounded formation 554 in the bottom piece 220 of the test device 100 accommodates a correspondingly rounded formation in the top piece 222 of the test device 100. The correspondingly rounded formation in the top piece 222 of the test device 100 receives the rounded bottom surface of the buffer container 226.

Figure 6:
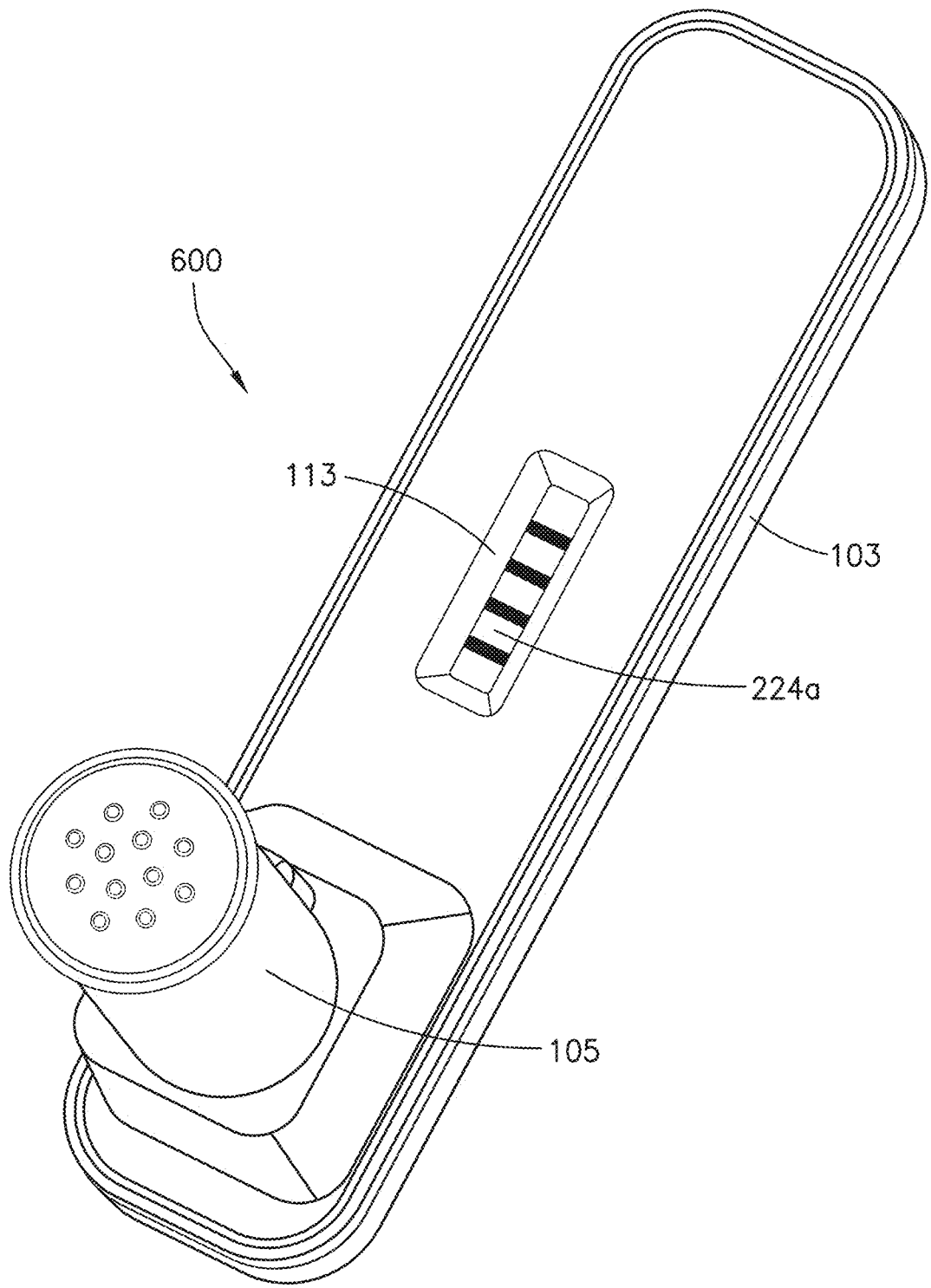
FIG. 6 is a perspective view showing another implementation of a test device.

FIG. 6 is a perspective view of another implementation of a test device 600 that is similar or identical in many respects to other test devices (see, e.g., 100 in FIG. 1B) discussed above. The main difference between the configuration shown in FIG. 6 and the configuration FIG. 1B, for example, is that the test strip 224a inside test device 600 (in FIG. 6) has more lines (e.g., test lines and/or control lines) that may appear during or as the result of a test being conducted than in FIG. 1B. Specifically, in the illustrated implementation, the test device 600 has four lines on its test strip 224a. However, it is possible for a test strip to have any number of lines. In the case of multiple analytes on one strip, for example, there is still only one control line, typically, and multiple test lines with each analyte being a test line.

FIG. 7A is a perspective view of yet another implementation of a test device 700 that is similar or identical in many respects to the test devices (see, e.g., 100 in FIG. 1B) discussed above. The main difference between the configuration shown in FIG. 7A and certain other test devices discussed above is that there are two test strips 724A, 724B in the test device 700 of FIG. 7A, instead of only one. In a typical implementation, each of two test strips is configured to test for a different condition than the other. For example, in one implementation, one of the test strips may be for testing for Covid and the other test strip may be for testing for influenza Type A and Type B. In another exemplary implementation, one of the test strips may be for testing for influenza A and B and the other may be for testing for Respiratory Syncytial Virus (RSV). Other combinations of test strips, including different types of test strips, are possible.

The two tests strips 724A, 724B are arranged side-by-side and parallel to one another. The test device 700 is configured, therefore, to accommodate the two test strips 724A, 724B instead of just one. This includes provisions for holding the two test strips 724A, 724B inside the test device 700. It also includes providing a test results viewing opening 713 in the top piece 722 of test device 700 that is sufficiently large (wide) that the test and control lines portion of both test strips 724A, 724B, arranged side-by-side can be seen. The side-by-side arrangement of tests strips facilitates easy assessment of test results—for multiple tests—simultaneously (either visually or using a reader). If several diseases share similar symptoms, for example, Flu A, Flu B, Covid, and RSV; then a FluA/B/Cov/RSV combo test can quickly give a user who exhibit symptoms exactly what he/she has.

Figure 7B:
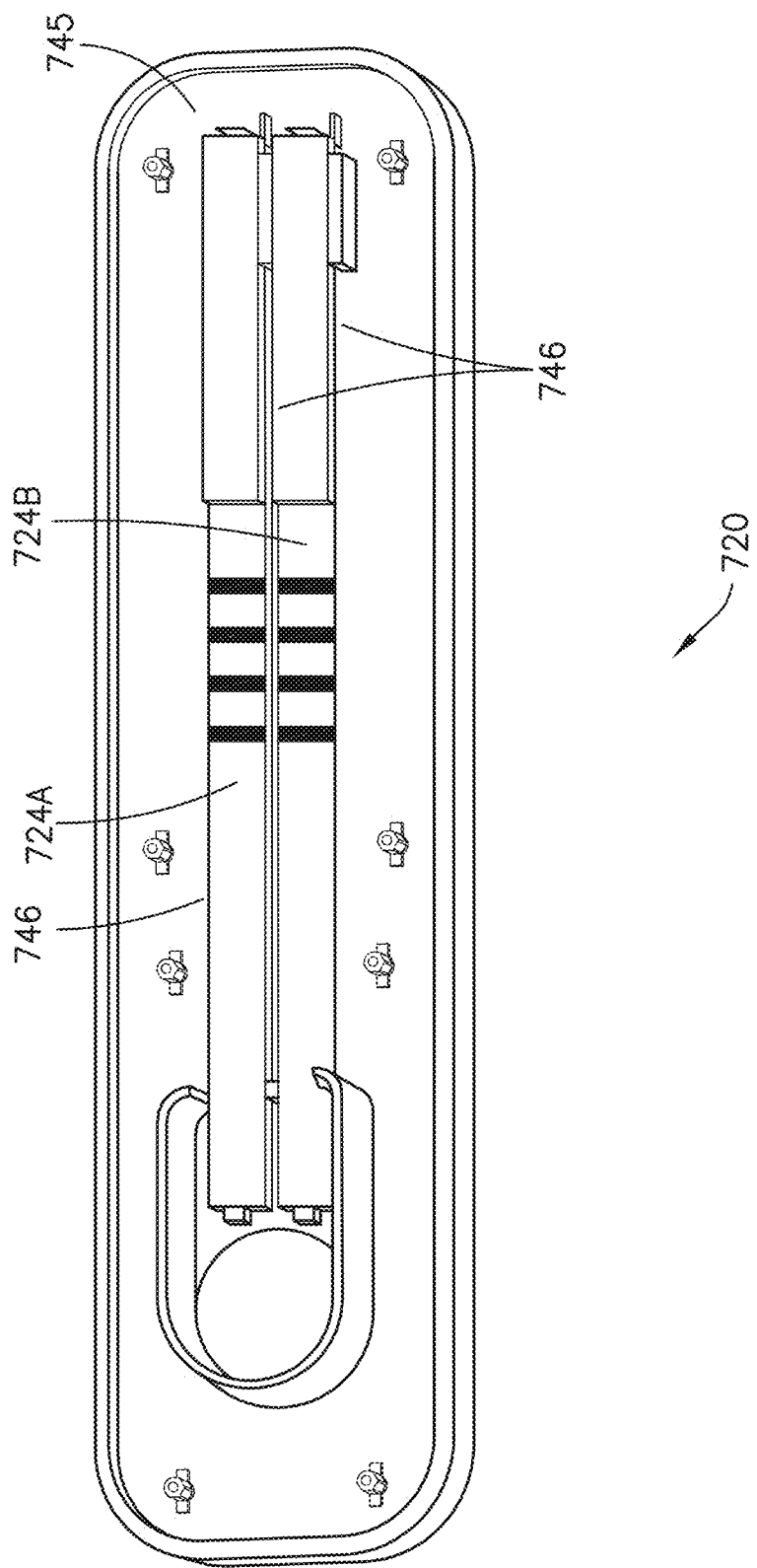
FIG. 7B is a perspective view showing the test device of FIG. 7A with its top piece removed.

FIG. 7B shows the bottom piece 720 of the test device 700 of FIG. 7A (with the top piece 722 removed) and the two test strips 724a, 724b in place resting atop the bottom piece 720. The test strips are held in place, aligned, parallel, and adjacent to each other by frame elements 744, 746, and 745.

In a typical implementation, the test device(s) disclosed herein are well suited for use as a standalone test device (with results being visually interpreted by the naked eye, for example), or together with a results reader that interprets the result by image capture and machine/artificial intelligence.

FIGS. 8A-8G shows a series of steps (1-7) involved in an exemplary implementation of using a test kit (that includes test device 100 and sample collector 102) together with a results reader 880 to interpret and/or report on the test results.

Figure 8A:
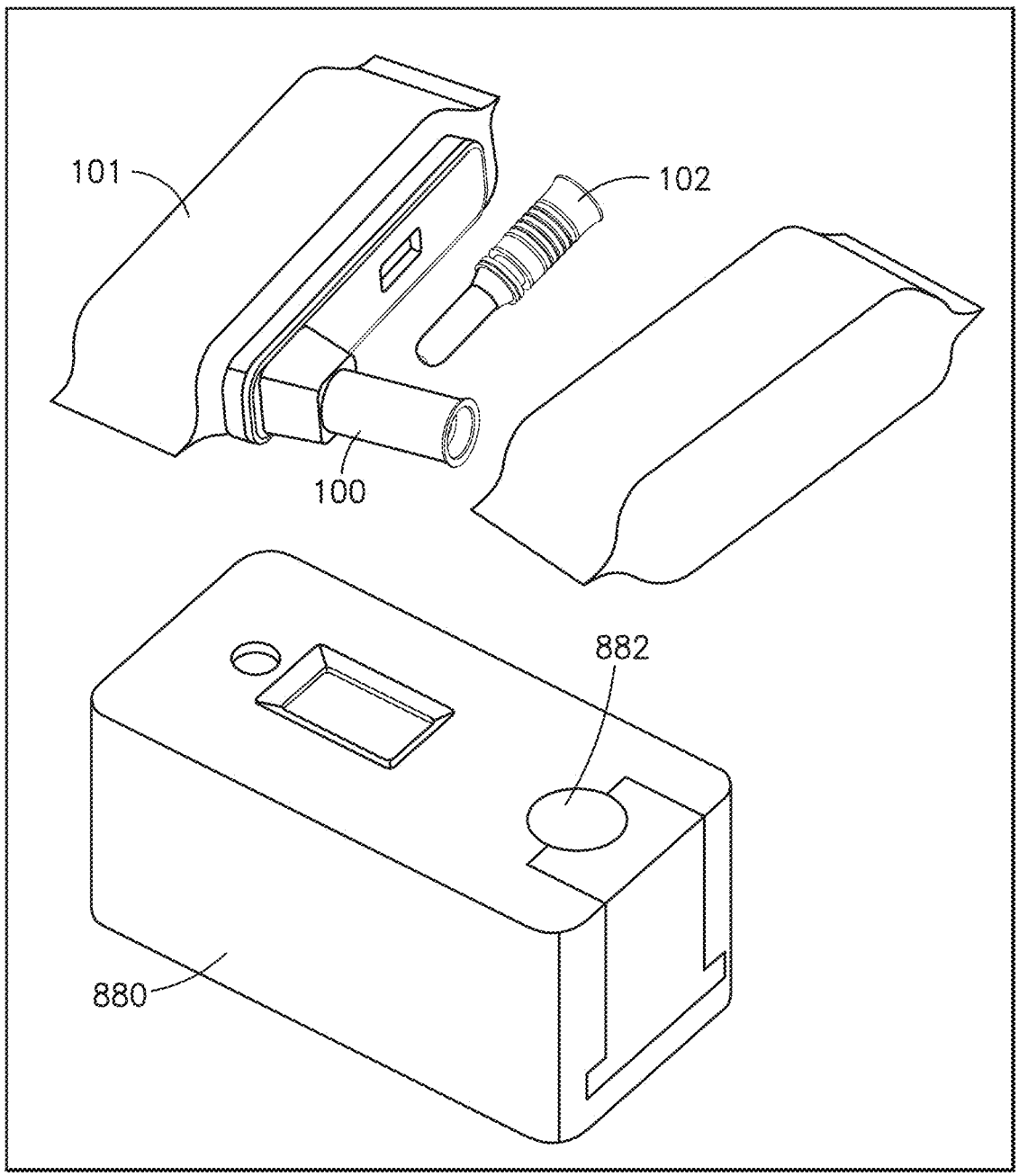
FIGS. 8A-8G shows a series of steps involved in an exemplary implementation of using test kit (that includes test device and sample collector) together with a results reader to interpret and/or report on the test results.
Figure 8B:
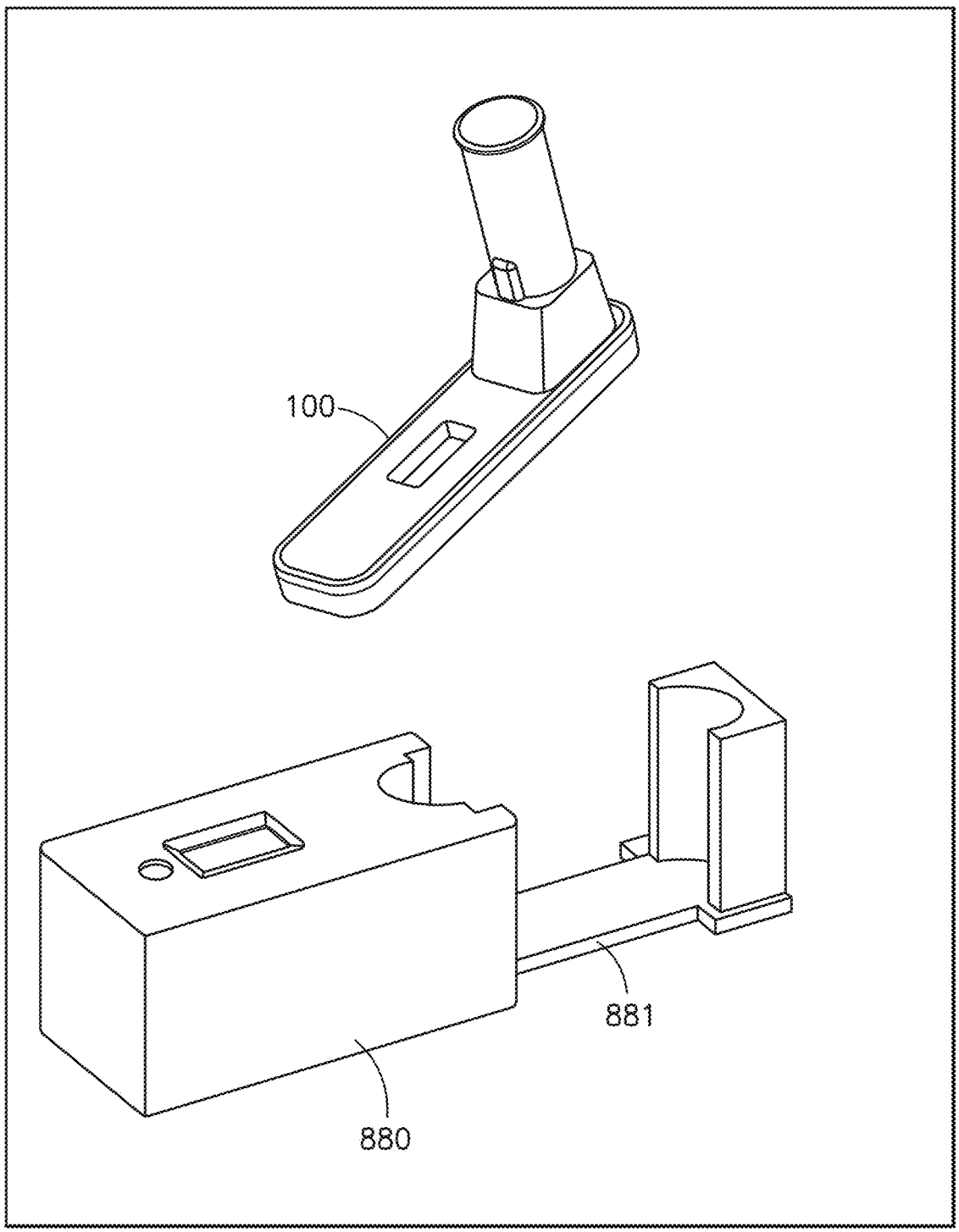
Figure 8C:
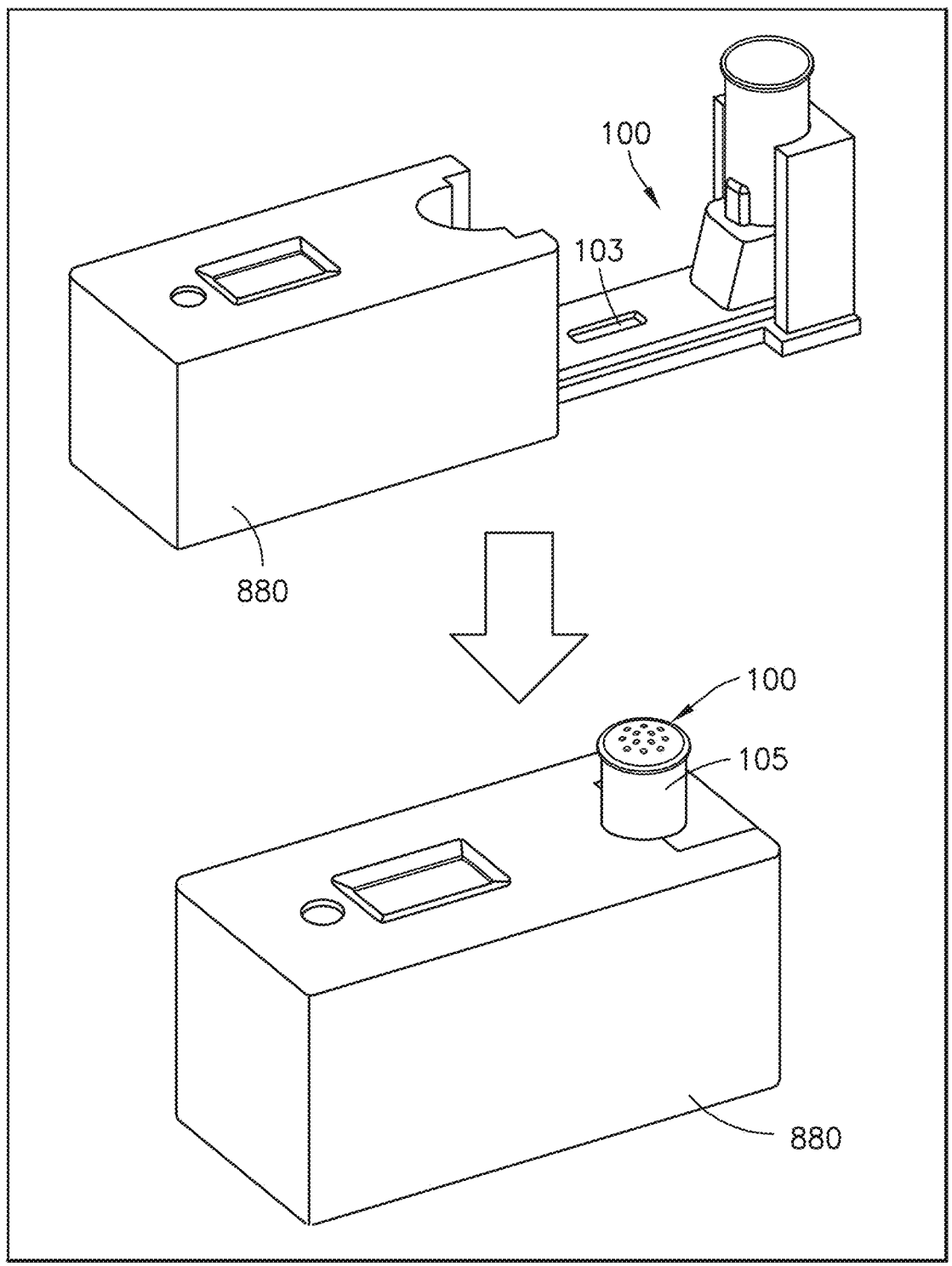

The steps include unsealing the package 101 (at step 1, FIG. 8A) and opening and powering the analyzer (reader) (at step 2, FIG. 8B). In this regard, the illustrated reader has a drawer that slides out of the reader housing to provide access to an internal compartment that can receive a substantial portion of the test device 100.

The test device 100 is placed (at step 3, see FIG. 8C) inside the drawer 881 and the drawer 881 is closed. Notably, once the drawer is closed, the entirety of the test device 100 is contained within the housing of the reader 880, except for the top of the hollow tubular portion 105 of the test device 100. The top of the hollow tubular portion 105 of the test device 100 extends out through a circular opening 882 in the upper surface of the housing of the test device 100. Configuring the test device 100 in the manner represented in FIG. 8C (step 3), for example, with its base 103 sitting atop the flat bottom surface of the drawer 881 and oriented substantially horizontally, facilitates the lateral flow of the analyte sample through the test strips inside the test device 100. This performance aspect is much better than if the test strips were disposed in a vertical orientation, where the lateral flow across the test strip might be fighting against gravity.

Figure 8E:
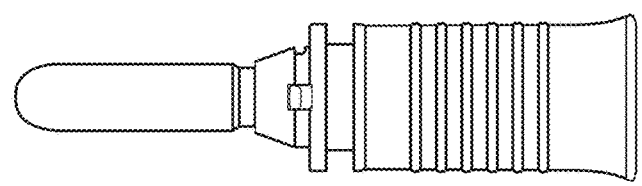
Figure 8D:
Figure 8D:
Figure 8D:
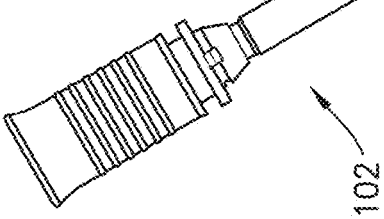
Figure 8F:
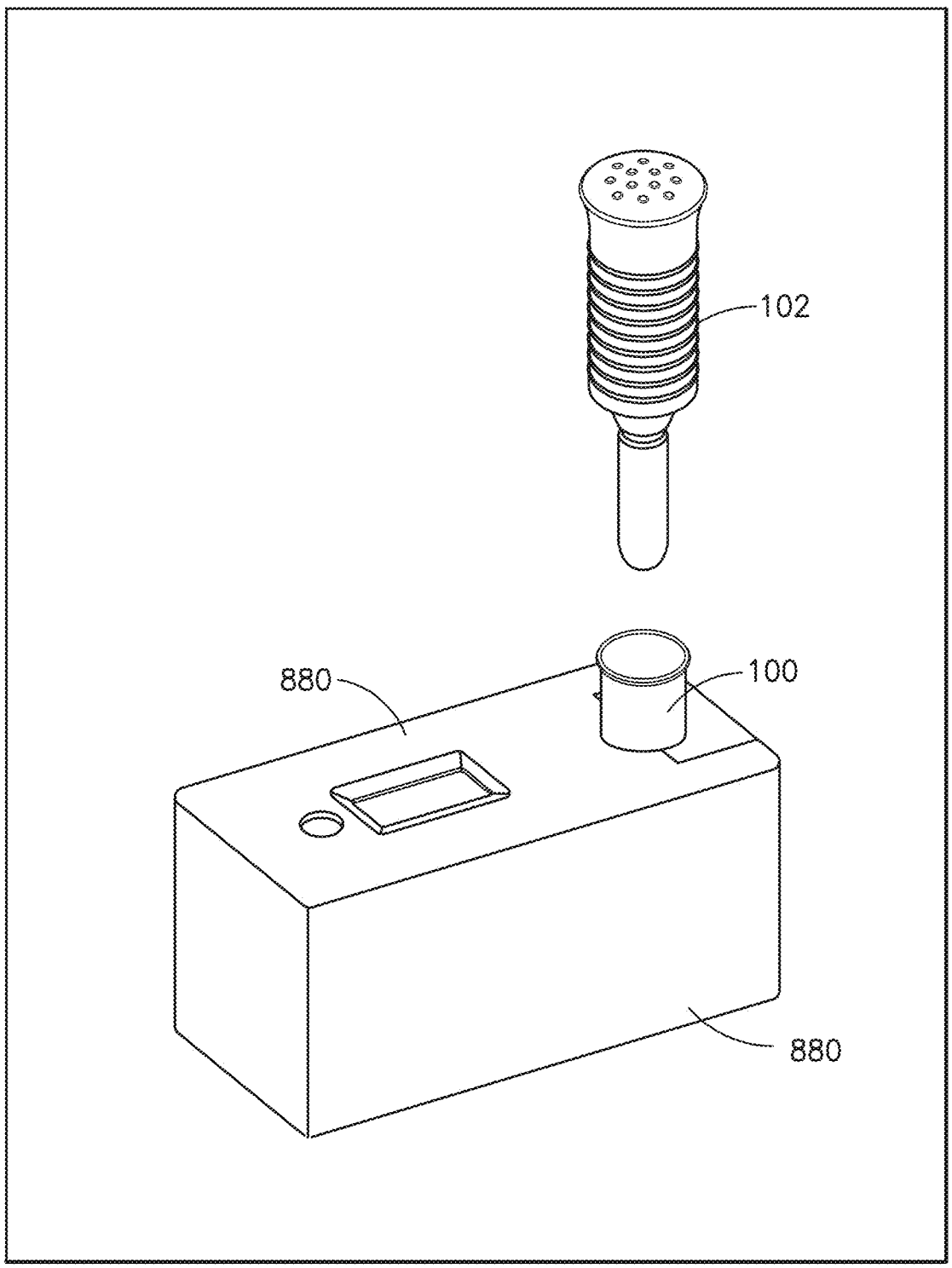
Figure 8G:
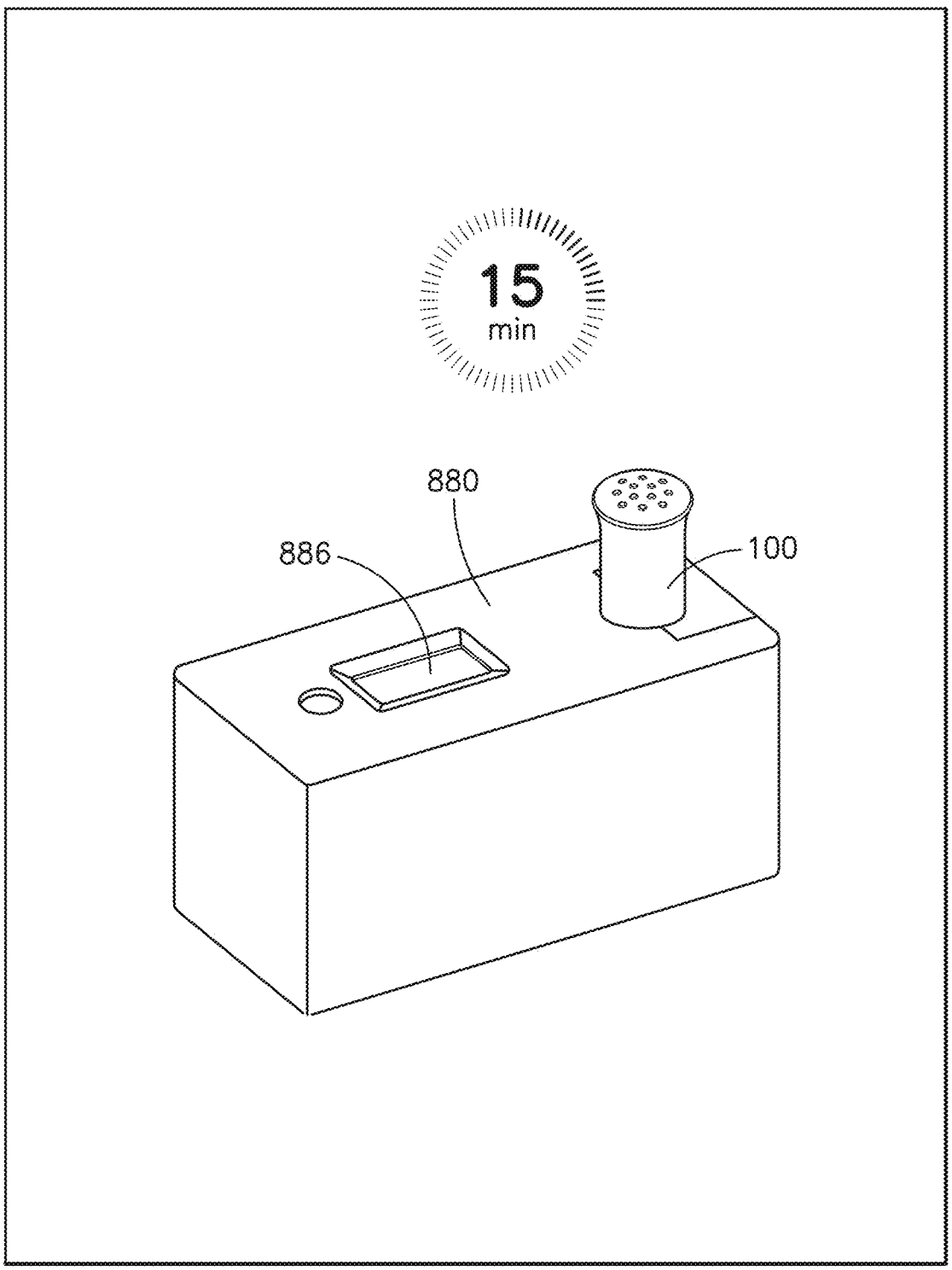

Next (in step 4, FIG. 8D), the cap is removed from the swab tip of the sample collector 102 and the sample is collected (in step 5, FIG. 8E). Then, the sample collector 102 with its swab is inserted into the hollow tubular portion 105 of the test device 100. After a certain amount of time (e.g., 15 minutes, as indicated in the illustrated implementation), the reader 880 captures an image of the portion of the test strips that are visible through the viewing opening 113 in the test device 100 (which is inside the reader 880), processes the image, and determines whether the image indicates a positive or negative result. The reader 880, in a typical implementation, provides an indication of the test result determination (e.g., on display screen 886).

In various implementations, the test device may be configured to facilitate proper alignment with a reader and/or to minimize optical pollution from ambient light when coupled to the reader. In this regard, the test device may include one or more structural features (e.g., a leaf spring, a tab, or other structural element) intended to engage with corresponding structural features (e.g., an indent, a bottom surface, or other structural feature) on the reader so that these aims may be achieved. These features can be incorporated into any implementation of a test device disclosed herein.

Figure 9:
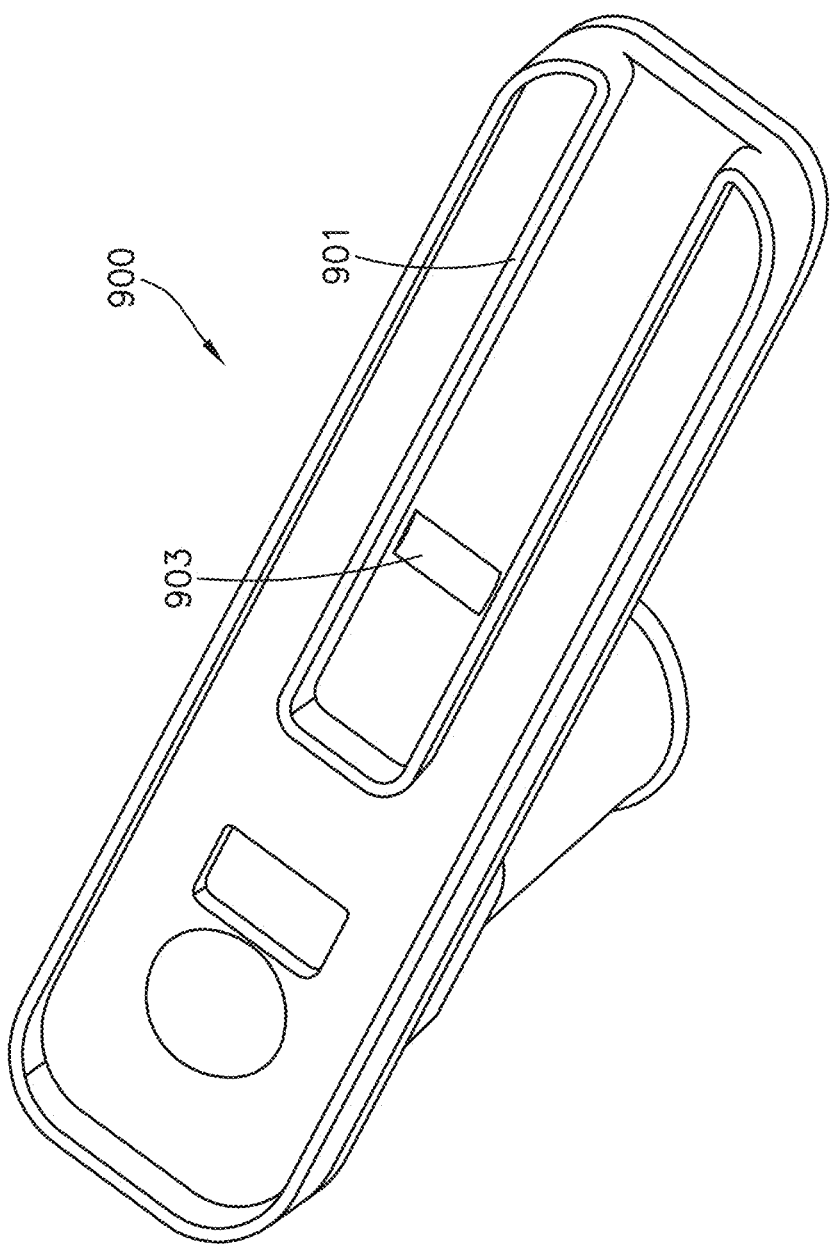
FIG. 9 is a bottom perspective view of an example of an exemplary test device.

FIG. 9 shows an example of a structural feature on the bottom surface of an exemplary test device 900 that includes a guide slot 901 formed from a raised projection 903 on the bottom surface of the test device 900 configured as shown. More specifically, the raised projection extends around a perimetrical edge of the bottom surface around most of the bottom surface of the test device 900 and extends inwardly from one section of the perimetrical edge to form two parallel walls (that act as sides of the guide slot 901) that meet at an inner wall (that acts as the back or stop in the guide slot 901). The guide slot 901 is configured to interact with a corresponding structure (e.g., a guide element) on a reader to ensure proper alignment and positioning of the test device 900 relative to the reader. Moreover, the guide slot 901 in a typical implementation interacts with the corresponding structure on the reader to limit left and right lateral movements in the test device 900 relative to the reader when engaged.

The bottom surface of the test device 900 further defines an indent 903 between the sides of the guide slot 901. The indent 903 extends laterally across a portion of the space between the sides of the guide slot 901 and has a curved profile in the longitudinal direction. The indent 903 is configured to interact with a corresponding structure (e.g., a spring leaf) on the reader to positively engage the test device 900 to the reader when the test device 900 is placed inside the reader. In a typical implementation, this helps keep the test device 900 engaged with the reader and prevent accidental or inadvertent disengagement of the test device from the reader. However, this resistance to removing the test device 900 from the reader is small enough that the user is able to remove the test device 900 relatively easily from the reader with the deliberate application of force. In some implementations, the corresponding structure (e.g., the spring leaf) on the reader is configured to urge the test device 900 in an upward direction so as to press the test device against the top of the receiver slot in the reader that receives the test device 900. This can help reduce or eliminate any pathways for undesirable light to reach the area of the test device where the test results can be read, which can be particularly important in implementations where machine reading of test results are produced. Additionally, moving the spring leaf into engagement with the indent provides the user with feedback (e.g., tactile and/or audible) that the test device 900 and the reader have been correctly and completely engaged.

Figure 10:
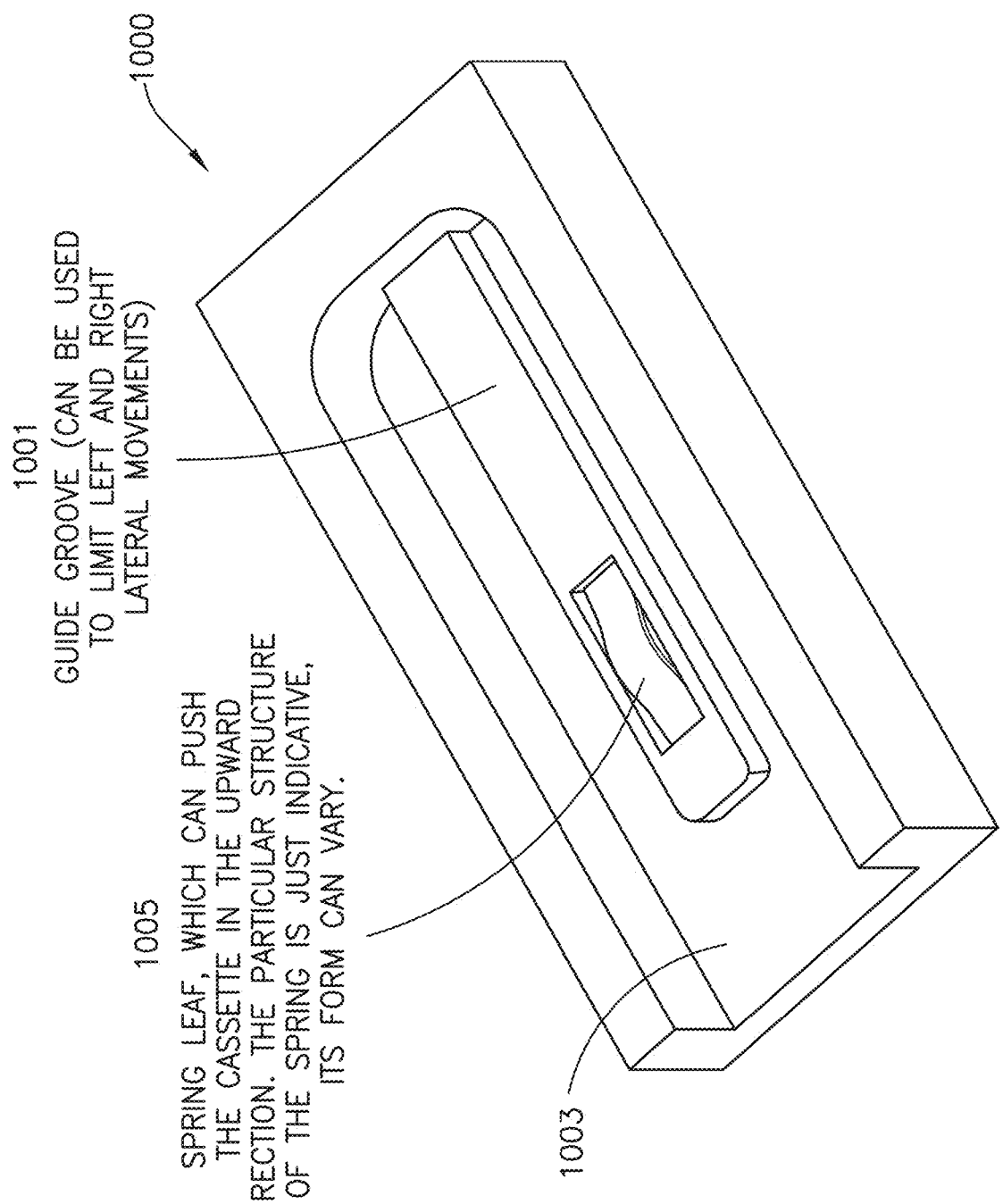
FIG. 10 is a partial cut view of a reader configured to mate with the test device of FIG. 9.

FIG. 10 is a partial cut view of a reader 1000 configured to mate with the test device 900 in FIG. 9. In this regard, the reader 1000 has a receiver slot 1003, a guide element 1001 inside the receiver slot, and a structure 1005 to positively engage the indent 903 on the test device of FIG. 9. The receiver slot 1003 in the illustrated implementation is sized and shaped to receive the base of the test device 900. In the illustrated example, the receiver slot 1003 is defined and surrounded on three sides by a raised wall with curved edges. The guide element 1001, in the illustrated implementation, is centrally disposed between the two parallel and longitudinal side walls of the receiver slot 1003 and extends from the back wall of the receiver slot forward. The guide element 1001, in the illustrated implementation, is in the form of an elongate upwardly extending projection that has a width that only slightly smaller than the distance between parallel walls of the guide slot 901 on the test device and a length that corresponds to a length of the guide slot 901. Structure 1005 (e.g., the leaf spring) is on the top surface of the guide element 1001 and is contoured to fit into the corresponding indent 903 on the test device 900 when the test device 900 is engaged to the reader. In this implementation, the leaf spring is configured to press upward on the test device 900 with the test device 900 so engaged.

Figure 11:
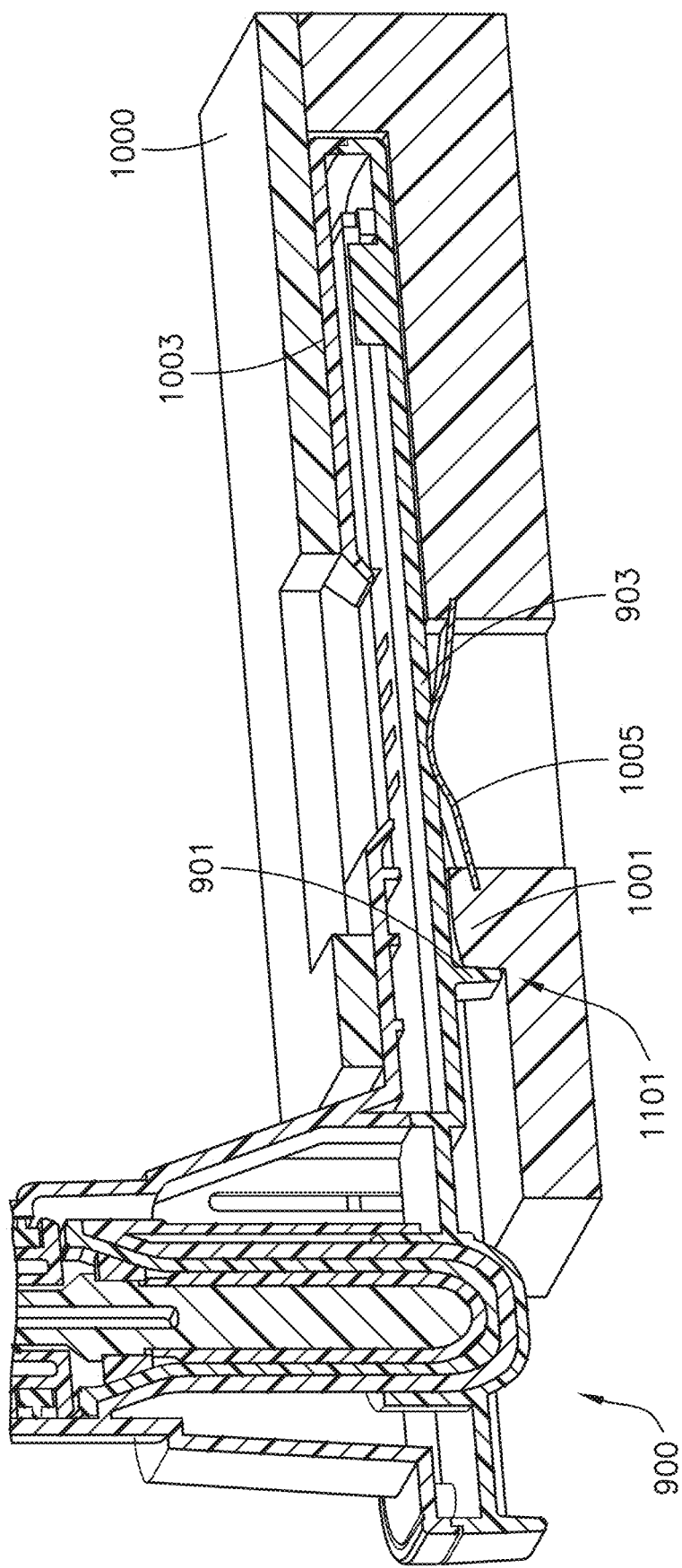
FIG. 11 is a cross-sectional side perspective view showing the test device of FIG. 9 coupled to the reader of FIG. 10.

FIG. 11 is a cross-sectional side perspective view showing test device 900 coupled to reader 1000. In the illustrated implementation, it can be seen that the base of the test device 900 is positioned within the receiver slot 1003 of the reader 1000, the back wall of the guide slot 901 on the test device 900 is in contact with end of the guide element 1001 of the reader (at 1101), and the leaf spring 1005 on the reader 1000 is engaged to and pressing up against the indent 903 on the test device 900 urging the test device 900 up against a top surface of the receiver slot 1003.

Figure 12:
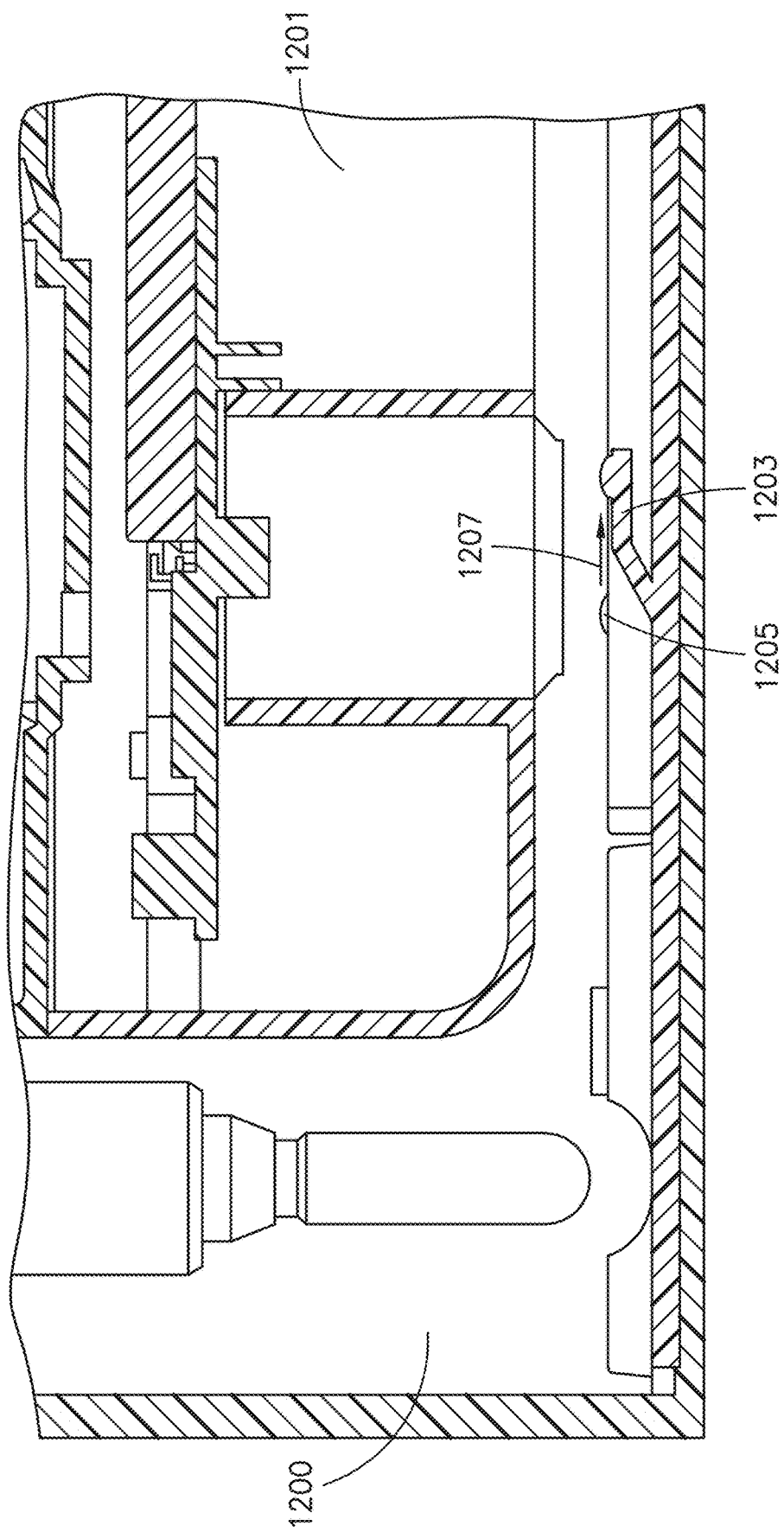
FIG. 12 is a cross-sectional side perspective view showing an alternative configuration of a test device coupled to a reader.

FIG. 12 shows an alternative configuration showing an exemplary test device 1200 coupled to a reader 1201. The illustrated reader 1201 has a small tab 1203 that extends from a bottom surface of the receiver slot in the reader 1201 to contact and press up against a bottom surface of the test device 1200 when the test device 1200 is inserted into the receiver slot of the reader. The illustrated tab 1203 has a first portion that extends in an angled, upward direction from the inner bottom surface of the receiver slot and a second portion that extends from a distal end of the first portion with an orientation that is substantially parallel to the inner bottom surface of the receiver slot. The tab 1203 may be configured to flex a bit in a downward direction as the test device 1200 moves into engagement with the reader 1201 and contacts the tab 1203. This slight flexing may enhance the upward force that the tab 1203 applies to the test device 1200 when the test device 1200 is engaged in the receiver slot. This causes the test device 1200 to press up against the upper inner surface 1205 of the receiver slot in the reader 1201. In a typical implementation, this configuration in FIG. 12 helps keep the test device 1200 engaged with the reader and prevent accidental or inadvertent disengagement of the test device from the reader. This resistance to removing the test device 1200 from the reader typically is small enough that the user is able to remove the test device 1200 relatively easily from the reader with the deliberate application of force. Additionally, by pressing the test device 1200 against the top of the receiver slot in the reader, according to the illustrated configuration, can help reduce or eliminate any pathways for undesirable light to reach the area of the test device 1200 where the test results can be read, which can be particularly important in implementations where machine reading of test results (e.g., by reader 1201) are produced. Other configurations are possible.

The test device 1200 in FIG. 12 has an indent 1205 on its bottom surface. The indent 1205 is configured to contact the top of the tab 1203 once the test device 1200 has been fully inserted into the reader 1201. The arrow 1207 in FIG. 12 shows the indent 1205 moving relative to the tab 1203 from a first position where the tab 1203 is not contacting the indent 1205 to a second position where the tab 1203 is contacting the indent 1205. The tab 1203 and the indent 1205 being in contact with one another tends to keep the test device 1200 and the reader 1201 coupled to one another (i.e.,  "locked" together). This further helps avoid the accidental separation of the test device 1200 from the reader 1201 (e.g., while test results are being read) unless separation is desired, in which case, the deliberate application of force by hand is typically sufficient to overcome the engagement between the tab 1203 and the indent 1205 in the second position mentioned above.

A number of embodiments of the invention have been described. Nevertheless, it will be understood that various modifications may be made without departing from the spirit and scope of the invention.

The systems and techniques disclosed herein are not limited to the applications specifically mentioned herein. In fact, the systems and techniques disclosed herein may be applied to virtually any kind of testing that involves lateral flow technology (e.g., lateral flow test strips). Some examples include Covid antigen and Flu AB testing, either used as a standalone test device (results are visually interpreted by naked eye), or together with a reader that interprets the result by machine/AI. However, the systems and techniques disclosed herein also can be expanded into testing other infectious disease, drugs of abuse, pregnancy. Moreover, the systems and techniques disclosed herein can be used to test all kinds of bodily fluid like saliva, urine, nasal, throat, feces, sweat, etc. They also can be used in surface testing, wastewater testing, and environmental testing.

A test device may be configured to hold any number of test strips including more than two test strips. Each test strip may be configured to test for something different than the others. Moreover, each test strip may be activated, so as to produce a useful test result, from one single sample and one single testing process occurring with that sample.

The test device can be provided as part of a kit that may include, for example, a package/container of any kind that contains the test device itself and may also include the sample collector. When so packaged (and prior to use), the buffer container is contained (e.g., with adhesive or friction) or otherwise integral with the test device. Moreover, when so packaged, the buffer container is sealed (e.g., by a frangible seal secured across and closing off its sealed upper opening). In some implementations, the kit may also include a reader for the test device. The reader, whether with a kit or not, may be configured to produce a visual output (e.g., on a built-in display screen or with simple light emitting diodes—e.g., red light for positive, green light for negative, yellow light for undetermined), an audible output (e.g., with one or more build-in audio speakers), a tactile output, or any other kind of output.

The physical configuration of the sample collector can vary considerably. For example, the sample collector handle could be longer. Other modifications are possible as well.

The physical configuration of the test device and its sub-components can vary as well. For example, the absolute and relative size of each of the hollow tubular portion, the flat base, the test strips, the transfer passage, and the buffer container can vary considerably. In some implementations, the buffer container may be provided as an element separate from the rest of the test device and the user may be provided with instructions for inserting the buffer container into the bottom of the hollow tubular portion of the test device. In some implementations, the test device may be openable (e.g., by separating by hand the bottom piece from the top piece—e.g., by pulling them apart, releasing a latch, etc.) and the test strips may be replaceable inside.

It should be noted that, although the buffer container is shown as a separate subcomponent that gets inserted (e.g., during test device manufacturing) into the receiver compartment of the test device. In some implementations, however, the buffer container may be integrated into (e.g., molded as part of) the top piece of the test device.

The test device may be able to be used with other kinds of readers beyond what is specifically mentioned herein.

The relative and absolute sizes, and relative positioning, of the various components and/or sub-components can vary considerably. A variety of materials may be suitable to form each component and/or sub-component.

In a typical implementation, each of the upper piece and the lower piece of the test device is made of a plastic material. In some implementations, each of these pieces may be molded (e.g., via an injection molding). In some implementations, the buffer container, too, may be made of plastic and manufactured using injection molding. Other materials and manufacturing processes may be utilized as well.

Although the hollow tubular portion of the test device advantageously helps guide the sample collector through the frangible seal and into the buffer container, in some implementations, the test device may not include the hollow tubular portion.

The buffer storage container, and the support structures for holding the buffer storage container, may vary. For example, the buffer storage container and associated support structures may be taller, shorter, wider, narrower, etc.

Depending on the type of specimen/sample type, the swab (and/or the rigid insert inside it) can be different from what is shown and described herein. More specifically, it can be changed to an appropriate shape and material for the different collection applications, such as a round and spongier material for saliva collection, a squared material that has properties to attract finer powder for surface collection, etc. So, when there are different kinds of tests, there may be different swabs and strips, without other major design changes. The paired reader (if used) can also stay the same.

Different types of test strips may be utilized. Some may have lines that are or become visible (e.g., with the naked eye). Others may be detectable some other way. For example, during fluorescence imaging, the item being inspected absorbs a shorter wavelength of light (usually ultraviolet (UV) light) that excites a specific fluorophore, causing it to release photons that fluoresce and emit light at a longer wavelength. The emitted light is then captured by the camera or other sensor of the reader. The scope of this application should apply to any kind of test strip, with any kind of detection scheme.

It should be understood that any relative terminology used herein, such as "upper," "lower," "above," "below," "front," "rear," etc. is solely intended to clearly describe the particular implementations being discussed and is not intended to limit the scope of what is described here to require particular positions and/or orientations. Moreover, terminology like "horizontal," "vertical," and the like, assume that the test device is sitting with its base flat against a horizontal support surface. If the test device is not sitting with its base on a horizontal support surface, then the surfaces, subcomponents, etc. described as being "horizontal," "vertical," or the like, would not be. These terms, therefore, should be considered as describing particular illustrated implementations and, unless otherwise indicated or claims, not otherwise limiting to the scope of the present application. Unless otherwise indicated and/or claimed, none of the relative terminology used herein should be construed to limit the scope of the present application. Additionally, terms such as substantially, and similar words, may be used herein. Unless otherwise indicated, substantially, and similar words, should be construed broadly to mean completely and almost completely (e.g., for a measurable quantity this might mean, for example (and without limitation), completely, 99% or more, 95% or more, 90% or more, 85% or more, 80% or more, etc.).

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations and/or processes are disclosed herein as occurring in a particular order, this should not be understood as requiring that such operations be performed in the particular order shown or in sequential order, or that all indicated operations be performed in order to achieve desirable results. In certain circumstances, multitasking or parallel processing may be advantageous.

Other implementations are within the scope of the claims.

What is claimed is:

1. A testing system comprising:
    a test device comprising:
        a base holding a test strip in a plane;
        a buffer storage container adjacent a first end of the test strip, wherein a top of the buffer storage container is higher than the plane of the base;
        a frangible seal across the top of the buffer storage container; and
        a transfer passage between the top of the buffer storage container and the first end of the test strip; and
    a sample collector for collecting a sample to be tested by the testing device,
    wherein the test device further comprises a hollow tubular portion that extends above and is aligned with the buffer storage container and the frangible seal across the top the buffer storage container,
    wherein the sample collector comprises:
        a handle portion; and
        a swab portion connected to the handle portion, and
    wherein the handle portion of the sample collector has an outer surface with an annular groove, the sample collector further comprising an O-ring inside the annular groove,
    wherein the transfer passage in the test device is configured to accommodate a flow of buffer liquid that is displaced from the buffer storage container by the swab portion of the sample collector, and mixed with a specimen sample from the swab portion of the sample collector and flows over a top edge of the buffer storage container, and
    wherein the transfer passage is further configured to deliver the buffer liquid and specimen sample mixture that flows over the top edge of the buffer storage container to the first end of the test strip.

2. The testing system of claim 1, wherein the hollow tubular portion of the test device is configured to receive the sample collector and to guide the handle portion of the sample collector so that the swab portion of the sample collector passes through the frangible seal and into the buffer container when the sample collector is pressed into the hollow tubular portion of the test device.

3. The testing system of claim 2, wherein the O-ring is configured to seal against an inner surface of the hollow tubular portion when the hollow tubular portion of the test device is guiding the handle portion of the sample collector.

4. The testing system of claim 1, wherein the buffer storage container has an inner diameter that is a tight fit around the swab portion of the sample collector.

5. The testing system of claim 1, wherein an inner surface of the buffer storage container comprises ribs or grooves that the swab portion of the sample collector rub against as the swab portion of the sample collector moves through the buffer container.

6. The testing system of claim 1, further comprising a buffer liquid contained inside the buffer storage container.

7. The testing system of claim 1, wherein the base of the test device comprises surfaces that define an opening to reveal a portion of the test strip inside the base.

8. The testing system claim 7, wherein the opening is not covered.

9. The testing system of claim 7, wherein the portion of the test strip revealed through the opening in the base is configured to produce at least one detectable indicator on the test strip indicating a test outcome.

10. The testing system of claim 1, wherein the at least one test strip comprises multiple test strips, wherein the multiple strips are arranged adjacent to one another, and wherein a portion of each respective one of the multiple test strips is revealed through the opening.

11. The testing system of claim 1, wherein the buffer container is adhered to, press fit into, or integrally molded into the testing device.

12. The testing system of claim 1, further comprising:
a package or container containing the test device and the sample collector.

13. The testing system of claim 1, wherein the swab portion of the sample collector is configured to tear through the frangible seal and fit into the buffer storage container, wherein the swab portion of the sample collector and the test device are configured such that, when the swab portion of the sample collector moves past the torn frangible seal and into the buffer storage container, the swab portion of the sample collector displaces the buffer liquid from the buffer storage container, such that the displaced buffer liquid flows up towards an opening at the top of the buffer storage container, moving past the swab portion of the sample collector in a direction that is opposite a direction in which the swab portion of the sample collector is moving further into the buffer storage container, wherein the displaced buffer liquid, after flowing past the swab portion of the sample collector and thereby mixing with the specimen sample on the swab portion of the sample collector, exits the buffer storage container through the opening at the top of the buffer storage container and flows from the opening at top of the buffer storage container through the transfer passage to the first end of the test strip.

14. The testing system of claim 13, wherein the test device further comprises:
a receiver compartment,
wherein the buffer storage container is in a sealed condition inside the receiver compartment and adjacent the first end of the test strip, wherein the buffer storage container, in the sealed condition, is held in place within the test device with an outer bottom surface of the buffer storage container in direct physical contact with an inner bottom surface of the receiver compartment while the buffer storage container is in the sealed condition and with the buffer storage container having an axis that is perpendicular to the plane.

15. The testing system of claim 14, wherein the buffer storage container is held in place inside the receiver compartment by a friction fit or by an adhesive.

16. The testing system of claim 13, wherein the swab portion of the sample collector and the buffer storage container are configured such that when the swab portion of the sample collector is inserted into a portion of the buffer storage container, an entire outer circumferential perimeter of the swab portion of the sample collector contacts, and remains in contact with, an inner surface of the buffer storage container, thereby causing the swab portion to be squeezed and compressed as it is pushed down into the buffer storage container.

17. The testing system of claim 13, wherein the test device and the sample collector are configured such that as the sample collector moves down into the buffer container, the swab portion of the sample collector comes into contact with, and begins to displace, the buffer liquid inside the buffer container, wherein the displaced buffer liquid flows up and around sides of the swab portion of the sample collector as the swab portion of the sample collector moves deeper into the buffer storage container,
wherein a tight fit between the swab portion and the buffer storage container results in at least a portion of the displaced buffer liquid mixing with the specimen sample on the swab portion of the sample collector as the buffer liquid flows up and around the swab portion of the sample collector, squeezing past and/or flowing through the swab portion of the sample collector to facilitate transfer of the specimen sample from the swab portion of the sample collector to the liquid buffer,
wherein an inner surface of the buffer storage container has ribs or grooves that the swab portion of the sample collector rubs against as the swab portion of the sample collector moves through the buffer storage container, wherein the rubbing further facilitates the transfer of the sample from the swab portion of the sample collector into the liquid buffer,
wherein as the swab portion of the sample collector moves further down into the buffer storage container further displacing the liquid buffer, a level of liquid buffer in the buffer storage container rises until, eventually, the level of liquid buffer in the buffer container gets so high that some of the liquid buffer, with a portion of the specimen sample, begins to spill over an upper edge of the buffer container,
wherein the liquid buffer, with the portion of the specimen sample, that spills over the upper edge of the buffer container falls through the transfer passage and onto the first end of the test strip.

18. A testing system comprising:
a test device comprising:
a base holding a test strip in a plane;
a buffer storage container adjacent a first end of the test strip, wherein a top of the buffer storage container is higher than the plane of the base;
a frangible seal across the top of the buffer storage container; and
a transfer passage between the top of the buffer storage container and the first end of the test strip; and a sample collector for collecting a sample to be tested by the testing device, wherein the sample collector comprises:
a handle portion; and
a swab portion connected to the handle portion
wherein the test device further comprises a hollow tubular portion that extends above and is aligned with the buffer storage container and the frangible seal across the top the buffer storage container,
wherein the transfer passage in the test device is configured to accommodate a flow of buffer liquid that is displaced from the buffer storage container by a swab portion of the sample collector, and mixed with a specimen sample from the swab portion of the sample collector and flows over a top edge of the buffer storage container, and
wherein the transfer passage is further configured to deliver the buffer liquid and specimen sample mixture that flows over the top edge of the buffer storage container to the first end of the test strip.

* * * * *